United States Patent [19]
Teng et al.

[11] Patent Number: 6,124,455
[45] Date of Patent: Sep. 26, 2000

[54] ARYL OR HETEROARYL AMIDES OF TETRAHYDRONAPHTHALENE, CHROMAN, THIOCHROMAN AND 1,2,3,4-TETRAHYDROQUINOLINE CARBOXYLIC ACIDS, HAVING AN ELECTRON WITHDRAWING SUBSTITUENT IN THE AROMATIC OR HETEROAROMATIC MOIETY, HAVING RETINOID-LIKE BIOLOGICAL ACTIVITY

[75] Inventors: Min Teng, Aliso Viejo; Tien T. Duong, Irvine; Roshantha A. Chandraratna, Mission Viejo, all of Calif.

[73] Assignee: Allergan Sales, Inc., Irvine, Calif.

[21] Appl. No.: 09/491,176

[22] Filed: Jan. 25, 2000

Related U.S. Application Data

[62] Division of application No. 09/173,574, Oct. 15, 1998, Pat. No. 6,034,244, which is a division of application No. 08/923,864, Sep. 4, 1997, Pat. No. 5,856,490, which is a division of application No. 08/562,000, Nov. 22, 1995, Pat. No. 5,675,024.

[51] Int. Cl.[7] ............... C07D 237/02; C07D 239/02; C07D 241/02; C07D 275/02; C07D 277/02

[52] U.S. Cl. ............... 544/224; 548/146; 548/182; 548/188; 548/195; 548/200; 548/206; 548/214; 548/225; 548/233; 548/240; 548/335.1; 548/335.5; 549/475; 549/480; 549/484; 549/487; 544/239; 544/298; 544/322; 544/335; 544/406

[58] Field of Search ............... 544/224, 239, 544/242, 298, 322, 335, 336, 406, 408; 548/146, 182, 188, 195, 200, 206, 214, 215, 225, 236, 240, 335.1, 335.5, 338.1, 341.5; 549/475, 480, 484, 487

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.26 |
| 4,485,252 | 11/1984 | Fuchs et al. | 560/8 |
| 4,539,154 | 9/1985 | Krebs | 260/410 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/552 |
| 4,826,984 | 5/1989 | Berlin et al. | 546/134 |
| 4,833,240 | 5/1989 | Maignana et al. | 536/55.2 |
| 4,855,320 | 8/1989 | Chatterjee et al. | 514/473 |
| 4,895,868 | 1/1990 | Chandraratna | 514/432 |
| 4,923,884 | 5/1990 | Chandraratna | 514/354 |
| 4,927,947 | 5/1990 | Chandraratna | 549/484 |
| 4,956,375 | 9/1990 | Oda et al. | 514/361 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |

(List continued on next page.)

FOREIGN PATENT DOCUMENTS

| | | |
|---|---|---|
| 170105A | of 0000 | European Pat. Off. . |
| 0098591 | 1/1984 | European Pat. Off. ...... C07D 333/54 |
| 0130795 | 1/1985 | European Pat. Off. ...... C07D 311/58 |
| 0176032 | 4/1986 | European Pat. Off. ...... C07C 65/38 |
| 0176033 | 4/1986 | European Pat. Off. ...... C07D 261/18 |
| 0253302 | 1/1988 | European Pat. Off. ...... C07D 213/16 |

(List continued on next page.)

OTHER PUBLICATIONS

A General Synthesis of Terminal and Internal Arylalkynes by the Palladium–Catalyzed Reaction of Alkynylzinc Reagents with Aryl Halides by Anthony O. King and Ei–i–chi, Negishi, *J. Org. Chem.*, (1978) 43/2: p. 358.

Conversion of Methyl Ketones into Terminal Acetylenes and (E)–Tri–substituted Olefins of Terpenoid Origin by Ei–ichi, et al., *J. Org. Chem.*, (1980) 45/12: p. 2526.

Sporn et al. in *J. Amer. Acad. Derm..*, (1986) 15:756–764.

"A Convenient Synthesis of Ethynylarenes and Diethynylarenes" by S. Takahashi et al. *Synthesis* (1980) p. 627–630.

Shudo et al. in *Chem. Phar. Bull.*, (1985) 33:404–407.

Kagechika et al. in *J. Med. Chem.*, (1988) 31:2182–2192.

(List continued on next page.)

*Primary Examiner*—C. S. Aulakh
*Attorney, Agent, or Firm*—Gabor L. Szekeres; Robert J. Baran; Martin A. Voet

[57] ABSTRACT

Compounds of the formula $$(R_3)o \underset{X}{\overset{R_1 \quad R_1}{\diagup}} \underset{(W)p}{\overset{(R_2)m}{\diagdown}} L-Y-A-B \atop (W)r$$

wherein the symbols have the meaning defined in the specification have retinoid-like biological activity.

2 Claims, No Drawings

U.S. PATENT DOCUMENTS

| | | | |
|---|---|---|---|
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,354,776 | 10/1994 | Chandratatna | 514/461 |
| 5,380,877 | 1/1995 | Chandraratna | 549/60 |
| 5,391,753 | 2/1995 | Chandraratna | 546/323 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,420,145 | 5/1995 | Shudo | 514/352 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,466,861 | 11/1995 | Dawson et al. | 560/100 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,525,618 | 6/1996 | Shudo et al. | 514/352 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,563,292 | 10/1996 | Sheh et al. | 560/255 |
| 5,591,858 | 1/1997 | Vuligonda et al. | 546/322 |
| 5,599,819 | 2/1997 | Chandraratna | 214/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligonda et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna et al. | 514/444 |
| 5,618,931 | 4/1997 | Beard et al. | 544/224 |
| 5,618,943 | 4/1997 | Vuligonda et al. | 546/342 |
| 5,648,385 | 7/1997 | Starrett, Jr. et al. | 514/513 |
| 5,648,503 | 7/1997 | Vuligonda et al. | 549/13 |
| 5,648,514 | 7/1997 | Johnson et al. | 560/102 |
| 5,654,469 | 8/1997 | Vuligonda et al. | 560/56 |
| 5,663,347 | 9/1997 | Chandraratna | 546/152 |
| 5,663,357 | 9/1997 | Teng et al. | 546/323 |
| 5,663,367 | 9/1997 | Vuligonda et al. | 549/4 |
| 5,672,710 | 9/1997 | Beard et al. | 548/188 |
| 5,675,024 | 10/1997 | Teng et al. | 549/405 |
| 5,675,033 | 10/1997 | Vuligonda et al. | 560/100 |
| 5,677,320 | 10/1997 | Chandraratna | 514/365 |
| 5,677,323 | 10/1997 | Chandraratna | 514/374 |
| 5,677,451 | 10/1997 | Chandraratna | 544/238 |
| 5,688,957 | 11/1997 | Teng et al. | 546/280.1 |
| 5,696,162 | 12/1997 | Chandraratna | 514/532 |
| 5,698,700 | 12/1997 | Song et al. | 546/282.1 |
| 5,856,490 | 1/1999 | Teng et al. | 546/165 |
| 6,034,244 | 3/2000 | Teng et al. | 546/309 |

FOREIGN PATENT DOCUMENTS

| | | | |
|---|---|---|---|
| 0272921 | 6/1988 | European Pat. Off. | C07D 213/80 |
| 0284261 | 9/1988 | European Pat. Off. | C07D 213/80 |
| 0284288 | 9/1988 | European Pat. Off. | C07D 401/04 |
| 0286364 | 12/1988 | European Pat. Off. | C07C 103/78 |
| 0303186 | 2/1989 | European Pat. Off. | |
| 0303915 | 2/1989 | European Pat. Off. | A61K 31/255 |
| 176034A | 4/1989 | European Pat. Off. | C07C 63/66 |
| 0315071 | 5/1989 | European Pat. Off. | C07C 63/66 |
| 0350846 | 7/1989 | European Pat. Off. | C07D 311/85 |
| 0412387 | 2/1991 | European Pat. Off. | C07C 317/14 |
| 0478787 | 3/1991 | European Pat. Off. | C07C 233/65 |
| 0514269 | 11/1992 | European Pat. Off. | C07C 257/08 |
| 0617020 | 9/1994 | European Pat. Off. | C07D 213/82 |
| 0619116 | 10/1994 | European Pat. Off. | A61K 31/19 |
| 0661259 | 5/1995 | European Pat. Off. | C07C 233/81 |
| 0661258 | 7/1995 | European Pat. Off. | C07D 65/19 |
| 0661261 | 7/1995 | European Pat. Off. | C07C 235/84 |
| 0718285 | 8/1996 | European Pat. Off. | C07C 403/20 |
| 3316932 | 11/1983 | Germany | C07C 63/66 |
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 85/00806 | 2/1985 | WIPO | A61K 31/00 |
| 85/04652 | 10/1985 | WIPO | A61K 31/19 |
| 91/16051 | 10/1991 | WIPO | A61K 31/44 |
| 92/06948 | 4/1992 | WIPO | C07C 69/86 |
| 93/03713 | 3/1993 | WIPO | A61K 31/07 |
| 93/11755 | 6/1993 | WIPO | A61K 31/07 |
| 93/21146 | 10/1993 | WIPO | C07C 69/76 |
| 94/14777 | 7/1994 | WIPO | C07D 231/54 |
| 95/04036 | 9/1995 | WIPO | C07C 403/20 |
| 96/05165 | 2/1996 | WIPO | C07C 57/50 |

OTHER PUBLICATIONS

Chemistry and Biology of Synthetic Retinoids by Marcia I. Dawson and William H. Okamura, published by CRC Press Inc., 1990, p. 334–335, 354.

Synthesis of 2,2'–Diacyl–1,1'–Biaryls. Regiocontrolled Protection of . . . by Mervic, et al, *J. Org. Chem.,* (1980) No. 45, p. 4720–4725.

A Dopamine Receptor Model and Its Application in the Design of a New Class of Rigid Pyrrolo[2,3–g]isoquinoline Antipsychotics, Gary L. Olson et al. *American Chemical Societe,* (1981) 24/9:1026–1031.

6.2.3 Conformational Restriction, Williams, et al., *Drug Discovery and Development,* The Humana Press, (1987) pp. 54–55.

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology,* (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology,* (1991) 96/3:.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991), 34:2579–2588.

"Synthesis and Evaluationof New Pretoein Tyrosine Kinase Inhibitors. Part 1. Pyridine–Containing Stilbenes and Amides" by Cushman, Mark et al. *Bioorganic & Medicinal Chemistry Letters,* (1991) 1/4:211–214.

"Di– and Tri–methoxystyryl Derivatives of Heterocyclic Nitrogen Compounds" by Bahner,C. T. et al. *Arzneim–Forsch,/Drug Res,* (1981)31 (I), Nr. 3.

"Retinobenzoic acids. 3. Structure–Activity Relationships of Retinoidal Azobenzene–4–Carboxylic Acids and Stilbene–4– Carboxylic Acids" by H. Kagechika et al., *Journal of Medicinal Chemistry,* (1989), 32:1098–1108.

Eyrolles, L. et al. "Retinoid Antagonists: Molecular Design Based on the Ligand Superfamily Concept" *Med. Chem. Res.,* (1992) 2:361–367.

Liu, S. S. et al. "Systemic Pharmacokinetics of Acetylenic Retinoids in Rats", *Drug Metabolism and Disposition,* (1990) 18/6: 1071–1077.

Chemical Abstracts, vol. 122, No. 13, Mar. 27, 1995 abstract No. 151372m, (S. Kaku et al.).

Chemical Abstracts, vol. 117, No. 13, Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, Aug. 2, 1996, pp. 3035–3038, Min Teng et al.

Journal of Medicinal Chemistry, vol. 37, No. 10, May 13, 1994, pp. 1508–1517, Laurence Eyrolles.

Biochemical and Biophysical Research Communications, vol. 155 No. 1, 1988, pp. 503–508.

Chemical Abstracts. vol. 121, No. 9, 1994.

Database WPi, Section CH, Week 9416, Derwent Publications Ltd. London, GB; Class B05, AN 94–128759 and JP 6078266A, see English language abstract in Derwent.

Journal of Medicinal Chemistry, vol. 38, No. 16, Aug. 4, 1995, pp. 3163–3173.

Weiner, et al., "A phase I trial of topically applied trans –retinoic acid in cervical dysplasia–clinical efficacy", *Investigational New Drugs,* 4:241–244, 1996.

Jones, et al., "A dose–response study of 13–cis–retinoic acid in acne vulgaris", *British Jornal of Dermatology,* (1983) 108, 333–343.

Fekrat, et al., "The Effect of Oral 13–cis–retinoic Acid on Retinal Redetachment after Surgical Repair in Eyes with Proliferative Vitreoretinopathy", *Ophthalmology,* vol. 102, No. 3 (Mar. 1995), pp. 412–418.

Nagpal, et al., "Separation of Transactivation and AP1 Antagonism Functions of Retinoic Acid Receptor $\alpha^*$", *The Journal of Biological Chemistry,* 270/2 (1995): 923–927.

Allegretto, et al., "Transactivation Properties of Retinoic Acid and Retinoid X Receptors in Mammalian Cells and Yeast", *The Journal of Biological Chemistry,* vol. 268, No. 35 (Dec. 15, 1993), pp. 26625–26633.

Gruapner, et al., "6'–Substituted Naphthalene–2–Carboxylic Acid Analogs, A New Class of Retinoic Acid Receptor Subtype–Specific Ligands," *Biochemical and Biophysical Research Communications,* vol. 179, No. 3 (Sep. 30, 1991), pp. 1554–1561.

Moore, et al., "Retinoic Acid and Interferon in Human Cancer: Mechanistic and Clinical Studies," *Seminars in Hematology,* 31/4, Suppl 5 (Oct. 1994), pp. 31–37.

ARYL OR HETEROARYL AMIDES OF TETRAHYDRONAPHTHALENE, CHROMAN, THIOCHROMAN AND 1,2,3,4-TETRAHYDROQUINOLINE CARBOXYLIC ACIDS, HAVING AN ELECTRON WITHDRAWING SUBSTITUENT IN THE AROMATIC OR HETEROAROMATIC MOIETY, HAVING RETINOID-LIKE BIOLOGICAL ACTIVITY

1. CROSS REFERENCE TO RELATED APPLICATION

The present application is a divisional of application Ser. No. 09/173,574, filed on Oct. 15, 1998, to be issued as U.S. Pat. No. 6,034,244, which is a divisional of application Ser. No. 08/923,864, filed on Sep. 4, 1997 now U.S. Pat. No. 5,856,490, which is a divisional of application Ser. No. 08/562,000, filed on Nov. 22, 1995, now U.S. Pat. No. 5,675,024.

BACKGROUND OF THE INVENTION

1. Field of the Invention

The present invention relates to novel compounds having retinoid-like biological activity. More specifically, the present invention relates to amides formed between aryl or heteroryl amines and tetrahydronaphthalene, chroman, thiochroman and 1,2,3,4-tetrahydroquinoline carboxylic acids where at least one of the aromatic or heteroaromatic moieties of the amide bears an electron withdrawing substituent.

The compounds are agonists of RAR retinoid receptors.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non- inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T- Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

U.S. Pat. No. 4,740,519 (Shroot et al.), U.S. Pat. No. 4,826,969 (Maignan et al.), U.S. Pat. No. 4,326,055 (Loeliger et al.), U.S. Pat. No. 5,130,335 (Chandraratna et al.), U.S. Pat. No. 5,037,825 (Klaus et al.), U.S. Pat. No. 5,231,113 (Chandraratna et al.), U.S. Pat. No. 5,324,840 (Chandraratna) U.S. Pat. No. 5,344,959 (Chandraratna), U.S. Pat. No. 5,130,335 (Chandraratna et al.), Published European Patent Application Nos 0 170 105 (Shudo), 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 A1 (Klaus et al.), DE 3602473 A1 (Wuest et al., and the articles J. Amer. Acad. Derm. 15: 756–764 (1986) (Sporn et al.), Chem. Pharm. Bull. 33: 404–407 (1985) (Shudo et al.), J. Med Chem. 1988 31, 2182–2192 (Kagechika et al.), Chemistry and Biology of Synthetic Retinoids CRC Press Inc. 1990 p 334–335, 354 (Dawson et al.), describe or relate to compounds which include a tetrahydronaphthyl moiety and have retinoid-like or related biological activity. U.S. Pat. No. 4,391,731 (Boller et al.) describes tetrahydronaphthalene derivatives which are useful in liquid crystal compositions.

U.S. Pat. Nos. 4,980,369, 5,006,550, 5,015,658, 5,045,551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,399,561, 5,407,937, (assigned to the same assignee as the present application) and patents and publications cited therein, describe or relate to chroman, thiochroman and 1,2,3,4-tetrahydroquinoline derivatives which have retinoid-like biological activity. Still further, several co-pending applications and recently issued patents which are assigned to the assignee of the present application, are directed to further compounds having retinoid-like activity.

It is now general knowledge in the art that two main types of retinoid receptors exist in mammals (and other organisms). The two main types or families of receptors respectively designated the RARs and RXRs. Within each type there are subtypes; in the RAR family the subtypes are designated RAR$_\alpha$, RAR$_\beta$ and RAR$_\Gamma$, in RXR the subtypes are: RXR$_\alpha$, RXB$_\beta$ and RXR$_\Gamma$. It has also been established in the art that the distribution of the two main retinoid receptor types, and of the several sub-types is not uniform in the various tissues and organs of mammalian organisms. Accordingly, among compounds having agonist-like activity at retinoid receptors, specificity or selectivity for one of the main types or families, and even specificity or selectivity for one or more subtypes within a family of receptors, is considered a desirable pharmacological property.

The present invention provides compounds having retinoid-like biological activity and specifically compounds which are agonists of one or more RAR retinoid receptor subtypes.

SUMMARY OF THE INVENTION

The present invention covers compounds of Formula

Formula 1

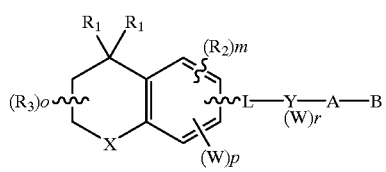

wherein X is S, O, NR' where R' is H or alkyl of 1 to 6 carbons, or

X is $[C(R_1)_2]_n$ where n is an integer between 0 and 2;

$R_1$ is independently H or alkyl of 1 to 6 carbons;

$R_2$ is hydrogen, or lower alkyl of 1 to 6 carbons;

$R_3$ is hydrogen, lower alkyl of 1 to 6 carbons or F;

m is an integer having the value of 0–2;

o is an integer having the value of 0–4;

p is an integer having the value of 0–2;

r is an integer having the value 0–2 with the proviso that when Z is O the sum of p and r is at least 1;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being optionally substituted with one or two $R_2$ groups;

W is a substituent selected from the group consisting of F, Br, Cl, I, $C_{1-6}$alkyl, fluoro substituted $C_{1-6}$ alkyl, $NO_2$, $N_3$, OH, $OCH_2OCH_3$, $OC_{1-10}$alkyl, tetrazol, CN, $SO_2C_{1-6}$-alkyl, $SO_2C_{1-6}$-alkyl, $SO_2C_{1-6}$-fluoro substituted alkyl, SO—$C_{1-6}$ alkyl, CO—$C_{1-6}$alkyl, $COOR_8$, phenyl, phenyl itself substituted with a W group other than with phenyl or substituted phenyl;

L is —(C=Z)—NH— or —NH—(C=Z)—

Z is O or S;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, where $R_7$ is an alkyl, cycloalkyl or alkenyl group containing 1 to 5 carbons, $R_8$ is an alkyl group of 1 to carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreo-retinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 1 in admixture with a pharmaceutically acceptable excipient.

In another aspect, this invention relates to processes for making a compound of Formula 1 which processes comprise reacting, in the presence of an acid acceptor or water acceptor, a compound of Formula 2 with a compound of Formula 3 or a compound of Formula 2a with a compound of Formula 3a where $X_1$ is OH, halogen, or other group which renders the —$COX_1$ group reactive for amide formation, and where the remaining symbols are defined as in connection with Formula 1.

Formula 2

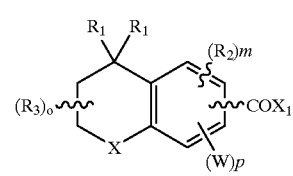

Formula 3

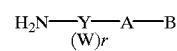

-continued

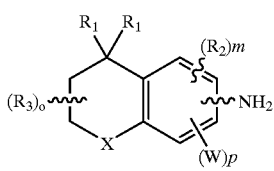

Formula 2a

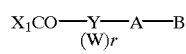

Formula 3a

Still further, the present invention relates to such reactions performed on the compounds of Formula 1 which cause transformations of the B group while the reaction product still remains within the scope of Formula 1.

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$, where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl.

Also, K may be —OR$_7$O— where R$_7$ is lower alkyl of 2–5 carbon atoms, straight chain or branched.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbol Y in Formula 1, the preferred compounds of the invention are those where Y is phenyl, pyridyl, 2-thiazolyl, thienyl, or furyl, more preferably phenyl. As far as substitutions on the Y (phenyl) and Y (pyridyl) groups are concerned, compounds are preferred where the phenyl group is 1,4 (para) substituted by the L and A-B groups, and where the pyridine ring is 2,5 substituted by the L and A-B groups. (Substitution in the 2,5 positions in the "pyridine" nomenclature corresponds to substitution in the 6-position in the "nicotinic acid" nomenclature.) In the preferred compounds of the invention there is no optional R$_2$ substituent on the Y group.

As far as the amide or carbamoyl function "L" is concerned which links the two cyclic portions of the molecule, L is preferably —CZ—NH—; in other words amide or carbamoyl compounds are preferred in accordance with the present invention where the carbonyl (CO—) or thiocarbonyl (CS—) group is linked to the condensed cyclic moiety.

With reference to the symbol X in Formula 1, compounds are preferred in accordance with the invention where X is [C(R$_1$)$_2$]$_n$, and n is 1, and also where X is O or S (chroman and thiochroman derivatives).

The RI groups are preferably H or CH$_3$. The R$_3$ group is preferably hydrogen. The A-B group of the preferred compounds is (CH$_2$)$_n$—COOH or (CH$_2$)$_n$—COOR$_8$, where n and R$_8$ are defined as above. Even more preferably n is zero and R$_8$ is lower alkyl, or n is zero and B is COOH or a pharmaceutically acceptable salt thereof. Referring now to the W group in Formula 1, this group is, generally speaking, an electron withdrawing group, which is present in the compounds of the invention either in the aromatic portion of the condensed ring system, or as a substituent of the aryl or heteroaryl group Y. Preferably the W group is present in the Y group, or both in the Y group and also in the aromatic portion of the condensed ring system. When the Z group is S (thioamides) a W group does not necessarily have to be present in the compounds of the invention, although preferably at least one W group is nevertheless present. In the aryl or heteroaryl Y moiety the W group is preferably located in the position adjacent to the A-B group; preferably the A-B group is in para position in the phenyl ring relative to the "amide" moiety, and therefore the W group is preferably in meta position relative to the amide moiety. Where the W group is also present in the aromatic portion of the condensed ring system, it preferably occupies the 8 position of the chroman or thiochroman nucleus with the Z=C—NH— group occupying the 6 position. In tetrahydronaphthalene compounds of the invention the Z=C—NH— group is preferably in the 2-position, and the W group is in the 3 or 4 position. Preferred w groups are F, $NO_2$, Br, I, $CF_3$, $N_3$, and OH. The presence of one or two fluoro substituents in the Y group is especially preferred. When the Y group is phenyl, the fluoro substituents preferably are in the ortho and ortho' positions relative to the A-B group, which is preferably COOH or $COOR_8$.

The most preferred compounds of the invention are shown in Table 1, with reference to Formulas 4 and 5.

TABLE 1

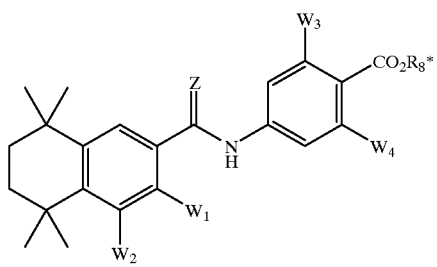

Formula 4

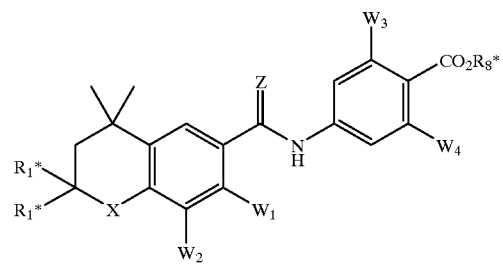

Formula 5

| Compound No. | Formula | $R_1$* | X* | $W_1$ | $W_2$ | Z | $W_3$ | $W_4$ | R8* |
|---|---|---|---|---|---|---|---|---|---|
| 1 | 4 | — | — | H | H | O | F | H | Et |
| 2 | 4 | — | — | H | H | O | F | H | H |
| 3 | 4 | — | — | F | H | O | H | H | Et |
| 4 | 4 | — | — | F | H | O | H | H | H |
| 5 | 4 | — | — | H | Br | O | F | H | Et |
| 6 | 4 | — | — | H | Br | O | F | H | H |
| 7 | 4 | — | — | OH | H | O | F | H | Et |

TABLE 1-continued

| Compound No. | Formula | $R_1$* | X* | $W_1$ | $W_2$ | Z | $W_3$ | $W_4$ | R8* |
|---|---|---|---|---|---|---|---|---|---|
| 8 | 4 | — | — | OH | H | O | F | H | H |
| 9 | 5 | H | O | H | Br | O | F | H | Et |
| 10 | 5 | H | O | H | Br | O | F | H | H |
| 11 | 5 | $CH_3$ | O | H | Br | O | F | H | Et |
| 12 | 5 | $CH_3$ | O | H | Br | O | F | H | H |
| 13 | 5 | $CH_3$ | O | H | $CF_3$ | O | F | H | Et |
| 14 | 5 | $CH_3$ | O | H | $CF_3$ | O | F | H | H |
| 15 | 5 | $CH_3$ | O | H | $N_3$ | O | F | H | Et |
| 16 | 5 | $CH_3$ | O | H | $N_3$ | O | F | H | H |
| 17 | 5 | $CH_3$ | O | H | $CF_3$ | O | F | F | $CH_3$ |
| 18 | 5 | $CH_3$ | O | H | $CF_3$ | O | F | F | H |
| 19 | 5 | $CH_3$ | O | H | I | O | F | H | Et |
| 20 | 5 | $CH_3$ | O | H | I | O | F | H | H |
| 21 | 5 | $CH_3$ | O | H | $CH_3$ | O | F | H | Et |
| 22 | 5 | $CH_3$ | O | H | $CH_3$ | O | F | H | H |
| 23 | 5 | $CH_3$ | S | H | H | O | F | H | Et |
| 24 | 5 | $CH_3$ | S | H | H | O | F | H | H |
| 25 | 4 | — | — | H | H | S | H | H | Et |
| 26 | 4 | — | — | H | H | S | H | H | H |
| 27 | 4 | — | — | H | H | S | F | H | Et |
| 28 | 4 | — | — | H | H | S | F | H | H |
| 29 | 4 | — | — | H | Br | O | $NO_2$ | H | $CH_3$ |
| 30 | 4 | — | — | H | Br | O | $NO_2$ | H | H |
| 31 | 5 | $CH_3$ | O | H | H | O | F | H | Et |
| 32 | 5 | $CH_3$ | O | H | H | O | F | H | H |
| 33 | 4 | — | — | OH | Br | O | F | H | Et |
| 34 | 4 | — | — | OH | Br | O | F | H | H |
| 35 | 4 | — | — | OH | Br | O | F | F | $CH_3$ |
| 36 | 4 | — | — | OH | Br | O | F | F | H |
| 37 | 4 | — | — | H | H | O | F | F | $CH_3$ |
| 38 | 4 | — | — | H | H | O | F | F | H |

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acme or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many disease for which these compounds are useful.

Assay of Retinoid-like Biological Activity

The retinoid-like activity of the compounds of the invention can be confirmed in assays wherein ability of the compound to bind to retinoid receptors is measured. As it is noted in the introductory section of this application for patent two main types of retinoic acid receptors (RAR and RXR) exist in mammals (and other organisms). Within each type there are sub-types ($RAR_\alpha$, $RAR_\beta$, $RAR_\Gamma$, $RXR_\alpha$, $RXR_\alpha$ and $RXR_\Gamma$) the distribution of which is not uniform in the various tissues and organs of mammalian organisms. Selective binding of only one or two retinoid receptor subtypes within one retinoid receptor family can give rise to beneficial pharmacological properties because of the varying distribution of the sub-types in the several mammalian tissues or organs. For the above-summarized reasons, binding of any or all of the retinoid receptors, as well as specific or selective activity in a receptor family, or selective or specific activity in any one of the receptor subtypes, are all considered desirable pharmacological properties.

In light of the foregoing the prior art has developed assay procedures for testing the agonist like activity of compounds in the $RAR_\alpha$, $RAR_\beta$ $RAR_\Gamma$, $RXR_\alpha$, $RXR_\beta$ and $RXR_\Gamma$ receptor subtypes. For example, a chimeric receptor transactivation assay which tests for agonist-like activity in the $RAR_\alpha$, $RAR_\beta$, $RAR_\Gamma$, and $RXR_\alpha$ receptor subtypes, and which is based on work published by Feigner P. L. and Holm M. (1989) Focus, 11 2 is described in detail in U.S. Pat. No. 5,455,265. The specification of U.S. Pat. No. 5,455,265 is expressly incorporated herein by reference.

A holoreceptor transactivation assay and a ligand binding assay which measure the ability of the compounds of the invention to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the ligand binding assay is also provided below.

Binding Assay

All binding assays were performed in a similar fashion. All six receptor types were derived from the expressed receptor type (RAR $\alpha$, $\beta$, $\Gamma$ and RXR $\alpha$, $\beta$, $\Gamma$) expressed in Baculovirus. Stock solutions of all compounds were prepared as 10 mM ethanol solutions and serial dilutions carried out into 1:1 DMSO; ethanol.

Assay buffers consisted of the following for all six receptor assays: 8% glycerol, 120 mM KCl, 8 mM Tris, 5 mM CHAPS 4 mM DTT and 0.24 mM PMSF, pH-7.4@ room temperature.

All receptor biding assays were performed in the same manner. The final assay volume was 250 $\mu$l and contained from 10–40 $\mu$g of extract protein depending on receptor being assayed along with 5 nM of [$^3$H] all-trans retinoic acid or 10 nM [$^3$H] 9-cis retinoic acid and varying concentrations of competing ligand at concentrations that ranged from $0$–$10^{-5}$ M. The assays were formatted for a 96 well minitube system. Incubations were carried out at 4° C. until equilibrium was achieved. Non-specific binding was defined as that binding remaining in the presence of 1000 nM of the appropriate unlabeled retinoic acid isomer. At the end of the incubation period, 50 $\mu$l of 6.25% hydroxyapitite was added in the appropriate wash buffer. The wash buffer consisted of 100 mM KCl, 10 mM Tris and either 5 mM CHAPS (RXR $\alpha$, $\beta$, $\Gamma$) or 0.5% Triton X-100 (RAR $\alpha$, $\beta$, $\Gamma$). The mixture was vortexed and incubated for 10 minutes at 4° C., centrifuged and the supernatant removed. The hydroxyapitite was washed three more times with the appropriate wash buffer. The receptor-ligand complex was adsorbed by the hydroxyapitite. The amount of receptor-ligand complex was determined by liquid scintillation counting of hydroxyapitite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a loglogit plot of the data. The $K_d$ values were determined by application of the Cheng- Prussof equation to the $IC_{50}$ values, the labeled ligand concentration and the $K_d$ of the labeled ligand.

The results of ligand binding assay are expressed in $K_d$ numbers. (See Cheng et al. Biochemical Pharmacology Vol. 22 pp 3099–3108, expressly incorporated herein by reference.)

Table 2 shows the results of the ligand binding assay for certain exemplary compounds of the invention.

TABLE 2

Ligand Binding Assay $K_d$ (nanomolar)

| Compound # | RARα | RARβ | RARΓ | RXRα | RXRβ | RXRΓ |
|---|---|---|---|---|---|---|
| 2 | 1.90 | 480.0 | 0.00 | 0.00 | 0.00 | 0.00 |
| 4 | 23.00 | 23.00 | 96.0 | 0.00 | 0.00 | 0.00 |
| 6 | 1.3 | 0.00 | 0.00 | 0.00 | 0.00 | 0.00 |
| 8 | 3.00 | 0.00 | 0.00 | 0.00 | 0.00 | 0.00 |
| 12 | 24.0 | 0.00 | 0.00 | 0.00 | 0.00 | 0.00 |
| 14 | 14.0 | 0.00 | 9.00 | 0.00 | 0.00 | 0.00 |
| 16 | 52.0 | 0.00 | 0.00 | 0.00 | 0.00 | 0.00 |
| 18 | 51.0 | 0.00 | 0.00 | 0.00 | 0.00 | 0.00 |
| 20 | 16.0 | 0.00 | 0.00 | 0.00 | 0.00 | 0.00 |
| 22 | 57.0 | 0.00 | 0.00 | 0.00 | 0.00 | 0.00 |
| 24 | 126.0 | 584 | 0.00 | 0.00 | 0.00 | 0.00 |
| 26 | 15 | 0.00 | 0.00 | 0.00 | 0.00 | 0.00 |
| 28 | 7.5 | 0.00 | 0.00 | 0.00 | 0.00 | 0.00 |
| 30 | 245.0 | 0.00 | 0.00 | 0.00 | 0.00 | 0.00 |
| 32 | 162.0 | 0.00 | 0.00 | 0.00 | 0.00 | 0.00 |
| 34 | 4.00 | 0.00 | 0.00 | 0.00 | 0.00 | 0.00 |
| 36 | 2.30 | 0.00 | 0.00 | 0.00 | 0.00 | 0.00 |
| 38 | 9.00 | 0.00 | 0.00 | 0.00 | 0.00 | 0.00 |

0.00 indicates value greater than 1000 nN (nanomolar)

As it can be seen from the test results summarized in Table 2, the therein indicated exemplary compounds of the invention bind specifically or selectively to RARα receptors.

Cancer Cell Line Assays
Materials and Methods
Hormones

All trans-Retinoic acid (t-RA) (Sigma Chemicals Co., St. Louis, Mo.) was stored at −70° C. Prior to each experiment the compound was dissolved in 100% ethanol at 1 mM and diluted in culture medium immediately before use. All experiments were performed in subdued light. Controls were assayed using the same concentration of ethanol as present in the experimental plates and this concentration of diluent had no effect in either assay.

Cells and Cell Culture

All cell lines, RPMI 8226, ME-180 and AML-193 were obtained from the American Type Culture Collection (ATCC, Rockville, Md.). RPMI 8226 is a human hematopoietic cell line obtained from the peripheral blood of a patient with multiple myeloma. The cells resemble the lymphoblastoid cells of other human lymphocyte cell lines and secrete α-type light chains of immunoglobulin. RPMI-8226 cells are grown in RPMI medium (Gibco) supplemented with 10% fetal bovine serum, glutamine and antibiotics. The cells were maintained as suspension cultures grown at 37° C. in a humidified atmosphere of 5% $CO_2$ in air. The cells were diluted to a concentration of $1\times10^5$/ml twice a week.

ME-180 is a human epidermoid carcinoma cell line derived from the cervix. The tumor was a highly invasive squamous cell carcinoma with irregular cell clusters and no significant keratinization. ME-180 cells were grown and maintained in McCoy's 5a medium (Gibco) supplemented with 10% fetal bovine serum, glutamine and antibiotics. The cells were maintained as monolayer cultures grown at 37° C. in a humidified atmosphere of 5% $CO_2$ in air. The cells were diluted to a concentration of $1\times10^5$/ml twice a week.

AML-193 was established from the blast cells classified as M5 Acute Monocyte Leukemia. The growth factor, granulocyte colony-stimulation factor (GM-CSF) was required to establish this cell line and growth factors are necessary for its continuous proliferation in chemically defined medium. AML-193 cells were grown and maintained in Iscove's modified Dulbecco's medium supplemented with 10% fetal bovine serum, glutamine and antibiotics with 5 μg/ml insulin (Sigma Chemical Co.) and 2 ng/ml rh GM-CSF (R and D Systems). The cells were diluted to a concentration of $3\times10^5$/ml twice a week.

Incorporation of $^3$H-Thymidine

The method used for determination of the incorporation of radiolabeled thymidine was adapted from the procedure described by Shrivastav et al. RPMI-8226 cells were plated in a 96 well round bottom microtiter plate (Costar) at a density of 1,000 cells/well. To appropriate wells, retinoid test compounds were added at the final concentrations indicated for a final volume of 150 μl/well. The plates were incubated for 96 hours at 37° C. in a humidified atmosphere of 5% $CO_2$ in air. Subsequently, 1 μCi of [5'-$^3$H]-thymidine (Amersham, U.K. 43 Ci/mmol specific activity) in 25 A1 culture medium was added to each well and the cells were incubated for an additional 6 hours. The cultures were further processed as described below.

ME-180 wells, harvested by trypsinization were plated in a 96 well flat bottom microtiter plate (Costar) at a density of 2,000 cells/well. The cultures were treated as described above for RPMI 8226 with the following exceptions. After incubation with thymidine the supernatant was carefully removed, and the cells were washed with a 0.5 mM solution of thymidine in phosphate buffered saline. ME180 cells were briefly treated with 50 μl of 2.5% trypsin to dislodge the cells from the plate.

AML-193 cells were plated in a 96 well round bottom microtiter plate (Costar) at a density of 1,000 cells/well. To appropriate wells, retinoid test compounds were added at the final concentrations indicated for a final volume of 150 μl/well. The plates were incubated for 96 hours at 37° C. in a humidified atmosphere of 5% $CO_2$ in air. Subsequently, 1 μCi of [5'-$^3$H]-thymidine (Amersham, U.K., 43 Ci/mmol specific activity) in 25 μl culture medium was added to each well and the cells were incubated for an additional 6 hours.

All cells lines were then processed as follows: the cellular DNA was precipitated with 10% trichloroacetic acid onto glass fiber filter mats using a SKATRON multi-well cell harvester (Skatron Instruments, Sterling Va.). Radioactivity incorporated into DNA, as a direct measurement of cell growth, was measured by liquid scintillation counting. The numbers represent the mean disintegrations per minute of incorporated thymidine from triplicate wells ±SEM.

In the above noted in vitro cell lines exemplary compounds 6, 8, 12, 14 and 20 of the invention caused significant decrease in the proliferation of the tumor cell lines (as measured by incorporation of radioactive labeled thymidine) in the $10^{-11}$ to $10^{-6}$ molar concentration range of the respective test compound.

SPECIFIC EMBODIMENTS

The compounds of this invention can be made by the synthetic chemical pathways illustrated here. The synthetic chemist will readily appreciate that the conditions set out here are specific embodiments which can be generalized to any and all of the compounds represented by Formula 1.

Generally speaking the process of preparing compounds of the invention involves the formation of an amide by the reaction of a compound of the general Formula 2 with a compound of general Formula 3, or by the reaction of a compound of general Formula 2a with a compound of general Formula 3a as these formulas are defined in the summary section of the present application for patent. Thus, as is noted above, a compound of Formula 2 is an acid or an "activated form" of a carboxylic acid attached to the aromatic portion of a tetrahydronaphthalene, (X=[C(R$_1$)$_2$]$_n$ and n is 1), dihydroindene ([C(R$_1$)$_2$]$_n$ where n is 0), chroman (X is 0), thiochroman (X is S), or tetrahydroquinoline (X is NR') nucleus. The carboxylic acid, or its "activated form" is attached to the 2 or 3 position of the tetrahyronaphthalene, and to the 6 or 7 position of the chroman, thiochroman or tetrahydroquinoline moieties.

In the preferred compounds of the invention the attachment is to the 2 position of tetrahydronaphthalene and to the 6 position of chroman, thiochroman or tetrahydroquinoline.

The term "activated form" of the carboxylic acid should be understood in this regard as such derivative of the carboxylic acid which is capable of forming an amide when reacted with a primary amine of Formula 3. In case of the "reverse amides" the activated form of a carboxylic acid is a derivative (Formula 3a) that is capable of forming an amide when reacted with a primary amine of Formula 2a. This, generally speaking, means such derivatives of a carboxylic acid which are normally known and used in the art to form amide linkages with an amine. Examples of suitable forms or derivatives for this purpose are acid chlorides, acid bromides, and esters of the carboxylic acid, particularly active esters, where the alcohol moiety of the ester forms a good leaving group. Presently most preferred as reagents in accordance with Formula 2 (or Formula 3a) are acid chlorides ($X_1$ is Cl). The acid chlorides of Formula 2 (or of Formula 3a) can be prepared by traditional methods from the corresponding esters ($X_1$ is for example ethyl) by hydrolysis and treatement with thionyl chloride ($SOCl_2$). The acid chlorides of Formula 2 (or of Formula 3a) can also be prepared by direct treatment of the carboxylic acids with thionyl chloride, where the carboxylic acid, rather than an ester thereof is available commercially or by a known synthetic procedure. The acid chlorides of Formula 2 (or of Formula 3a) are typically reacted with the amine of Formula 3 (or amine of Formula 2a) in an inert solvent, such as methylene chloride, in the presence of an acid acceptor, such as pyridine.

The carboxylic acids themselves in accordance with Formula 2 (or Formula 3a) are also suitable for amide formation when reacted with an amine, a catalyst (4-dimethylaminopyridine) in the presence of a dehydrating agent, such as dicyclohexylcarbodiimide (DCC) or more pereferably 1-(3-dimethylaminopropyl)-3-ethylcarbodiimide hydrochloride (EDC).

The carboxylic acids or the corresponding esters of Formula 2, are generally speaking, prepared as described in the chemical scientific or patent literature and the literature procedures for their preparation may be modified, if necessary, by such chemical reactions or processes which per se are known in the art. For example, generally speaking, 2,2, 4,4 and/or 2,2,4,4-substituted chroman 6-carboxylic acids and chroman 7-carboxylic acids are available in accordance with the teachings of U.S. Pat. Nos. 5,006,550, 5,314,159, 5,324,744, and 5,348,975, the specifications of which are expressly incorporated herein by reference. 2,2, 4,4 and/or 2,2,4,4-substituted thiochroman 6-carboxylic acids are available in accordance with the teachings of U.S. Pat. No. 5,015,658, the specifications of which is expressly incorporated herein by reference. 5,6,7,8-Tetrahydronaphthalene-2-carboxylic acids are, generally speaking, available in accordance with the teachings of U.S. Pat. No. 5,130,335, the specifications of which is expressly incorporated herein by reference.

Reaction Scheme 1

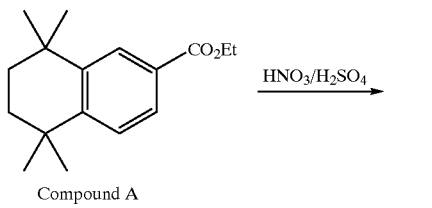

Compound A

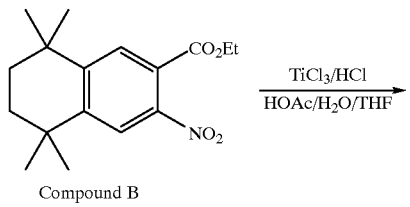

Compound B

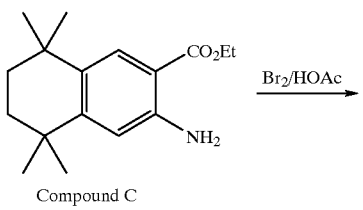

Compound C

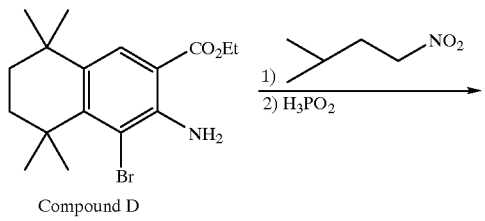

Compound D

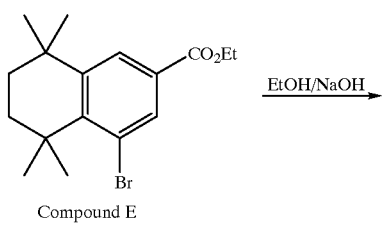

Compound E

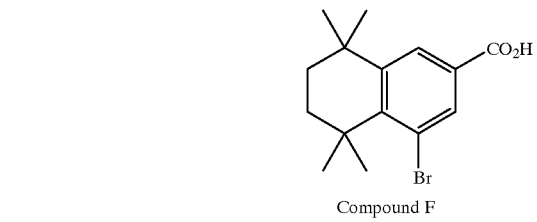

Compound C

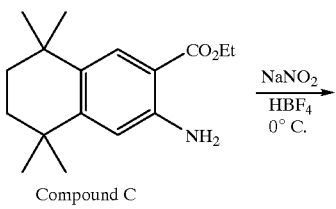

Compound F

15
-continued

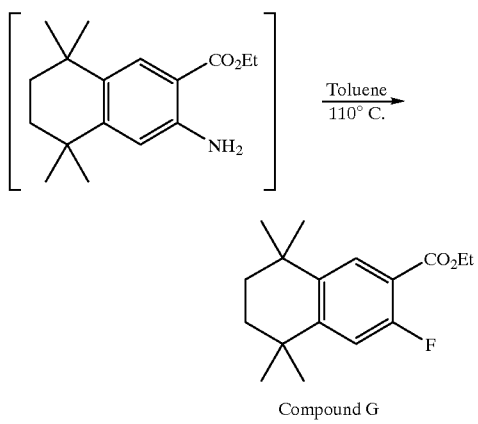

Compound G

Reaction Scheme 2

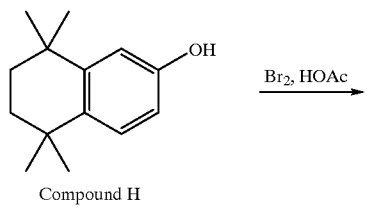

Compound H
Krause, J. G.
Synthesis 1972, p140

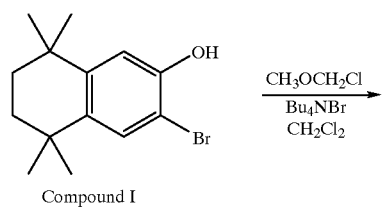

Compound I

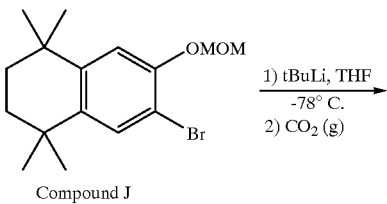

Compound J

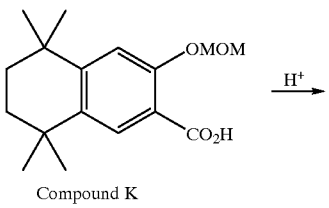

Compound K

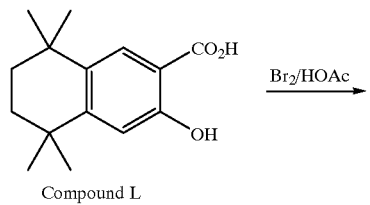

Compound L

16
-continued

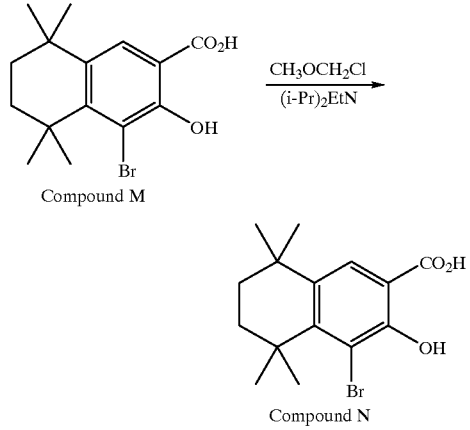

Compound M

Compound N

Reaction Schemes 1 and 2 provide examples for the synthesis of derivatives of 5,6,7,8-tetrahydro-5,5,8,8-tetramethylnaphthalene-2-carboxylic acid, which are within the scope of Formula 2 and which are reacted with an amine of Formula 3 to provide (5,6,7,8-tetrahydro-5,5,8,8-tetramethyl-naphthalene-2-yl)carbamoyl derivatives within the scope of Formula 1. Thus, as is shown in Reaction Scheme 1, ethyl 5,6,7,8-tetrahydro-5,5,8,8-tetramethylnaphthalene-2-carboxylate (Compound A) is nitrated to provide the corresponding 3-nitro compound (Compound B). The nitro group of Compound B is reduced to provide the corresponding 3-amino compound (Compound C) which is described in the publication Lehmann et al. Cancer Research, 1991, 51, 4804. Ethyl 5,6,7,8-tetrahydro-5,5,8,8-tetramethyl-3-aminonaphthalene-2-carboxylate (Compound C) is brominated to yield the corresponding 4-bromo derivative (Compound D), which is converted by treatment with isoamylnitrite and reduction with $H_3PO_2$, to ethyl 5,6,7,8-tetrahydro-5,5,8,8-tetramethyl-4-bromonaphthalene-2-carboxylate (Compound E). Saponification of Compound E yields 5,6,7,8-tetrahydro-5,5,8,8-tetramethyl-4-bromonaphthalene-2-carboxylic acid (Compound F) which is used as a reagent in accordance with Formula 2. Ethyl 5,6,7,8-tetrahydro-5,5,8,8-tetramethyl-3-aminonaphthalene-2-carboxylate (Compound C) is also diazotized and reacted with $HBF_4$ to provide ethyl 5,6,7,8-tetrahydro-5,5,8,8-tetra- methyl-3-fluoronaphthalene-2-carboxylate (Compound G) which serves either per se or after saponification as a reagent in accordance with Formula 2.

5,6,7,8-Tetrahydro-5,5,8,8-tetramethyl-2-hydroxy- naphthalene (Compound H, available in accordance with the publication Krause Synthesis 1972 140), is the starting material in the example shown in Reaction Scheme 2. Compound H is brominated to provide the corresponding 3-bromo compound (Compound I) which is thereafter protected in the hydroxyl function by treatment with methoxymethyl chloride (MOMCl) to yield 5,6,7,8-tetrahydro-5,5,8,8-tetramethyl-3-methoxymethoxy-2-bromonaphthalene (Compound J). Compound J is reacted with t-butyllithium and carbon dioxide to provide the corresponding carboxylic acid (Compound K) from which the methoxymethyl protecting group is re- moved by acid to give 5,6,7,8-tetrahydro-5,5,8,8-tetra- methyl-2-hydroxynaphthalene-3-carboxylic acid (Compound L). Compound L is brominated to yield 5,6,7,8-tetrahydro-5,5, 8,8-tetramethyl-1-bromo-2-hydroxynaphthalene-3-carboxylic acid (Compound M). Compound L and Compound serve as reagents in accordance with Formula 2. The hydroxy group of Compound M is protected for further transformations with methoxymethyl chloride (MOMCl) in the presence of base, yielding 5,6,7,8-tetrahydro- 5,5,8,8-tetramethyl-1-bromo-2-methoxymethoxynaphthalene-3-carboxylic acid (Compound N).

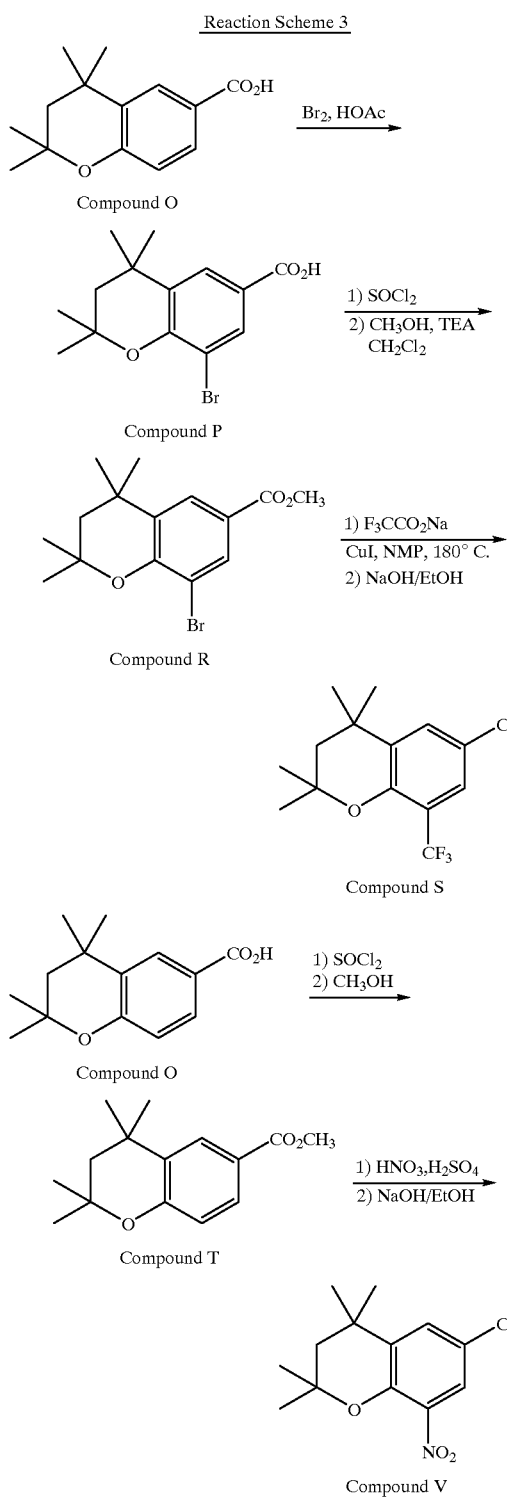

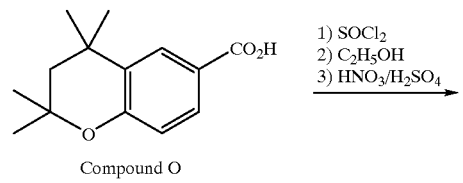

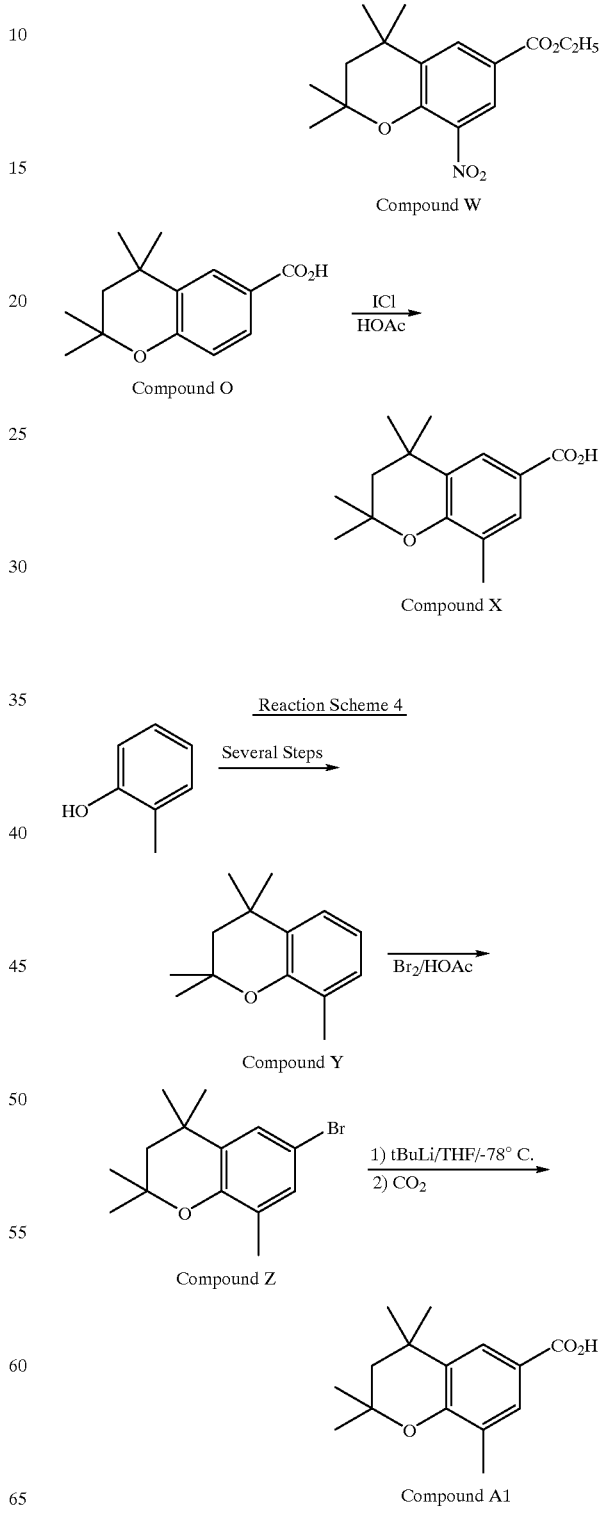

Reaction Scheme 5

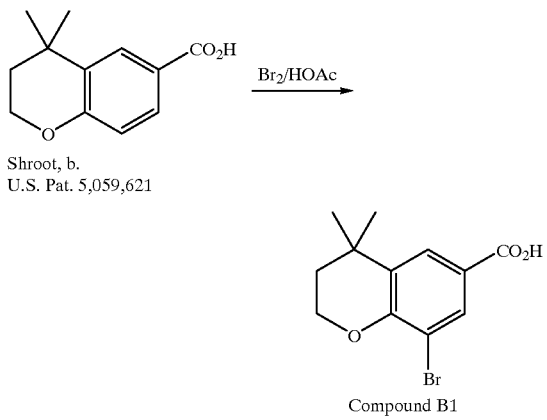

Compound B1

Reaction Schemes 3, 4 and 5 provide examples for the synthesis of derivatives of 2,2,4,4 and 4,4-substituted chroman-6-carboxylic acids which can serve as reagents in accordance with Formula 2 for the synthesis of the carbamoyl (amide) compounds within the scope of the present invention. Thus, referring now to Reaction Scheme 3, 2,2, 4,4-tetramethylchroman-6-carboxylic acid (Compound O, see U.S. Pat. No. 5,006,550) is brominated with bromine in acetic acid to yield the corresponding 8-bromo derivative (Compound P). Compound P is converted to the acid chloride by treatment with thionyl chloride, and the resulting acid chloride is suitable for reaction with an amine of Formula 3 to provide the carbamoyl (amide) compounds of the invention. The acid chloride is also reacted with an alcohol (methanol) in the presence of base to yield the corresponding ester, methyl 2,2,4,4-tetramethyl-8-bromochroman-6-carboxylate (Compound R). The bromo function of Compound R is converted to a trifluoromethyl function by treatment with sodium trifluoroacetate in the presence of cuprous iodide catalyst and 1-methyl-2-pyrrolidinone (NMP), and the carboxylate ester group is saponified to yield 2,2,4,4-tetramethyl-8-trifluoromethylchroman-6-carboxylic acid (Compound S). Compound S is within the scope of Formula 2 and is suitable per se or as the acid chloride or in other "activated" form to react with the amines of Formula 3 to yield the carbamoyl (amide) compounds of the invention. 2,2,4,4-Tetramethylchroman-6-carboxylic acid (Compound O) is also converted to the methyl ester (Compound T) which is then nitrated to yield 2,2,4,4-tetramethyl-8-nitrochroman-6-carboxylic acid (Compound V), still another reagent within the scope of Formula 2. Moreover, in the example further shown in Reaction Scheme 3, 2,2,4,4-tetramethylchroman-6-carboxylic acid (Compound O) is converted to the ethyl ester and nitrated thereafter to yield ethyl 2,2,4,4-tetramethyl-8-nitrochroman-6-carboxylate (Compound W). Still further, Compound O is reacted with ICl to yield 2,2,4,4-tetramethyl-8-iodochroman-6-carboxylic acid (Compound X).

In accordance with the example shown in Reaction Scheme 4, 2-methylphenol is subjected to a series of reactions in accordance with the teachings of U.S. Pat. No. 5,045,551 (incorporated herein by reference) to yield 2,2,4,4,8-pentamethylchroman (Compound Y). Compound Y is brominated with bromine in acetic acid to give 2,2,4,4,8-pentamethyl-6-bromochroman (Compound Z) which is reacted with t-butyl lithium and thereafter with carbon dioxide to give 2,2,14,4,8-pentamethylchroman-6-carboxylic acid (Compound $A_1$).

Reaction scheme 5 illustrates the synthesis of 4,4-dimethyl-8-bromochroman-6-carboxylic acid (Compound $B_1$) by bromination of 4,4,-dimethyl-chroman-6-carboxylic acid which is available in accordance with the teachings of U.S. Pat. No. 5,059,621, the specification of which is incorporated herein by reference. 2,2,4,4,8-Pentamethylchroman-6-carboxylic acid (Compound $A_1$) and 4,4,-dimethyl-8-bromochroman-6-carboxylic acid (Compound $B_1$) serve as reagents, either per se, or as the corresponding acid chlorides (or other "activated" form), in accordance with Formula 2 for the synthesis of the carbamoyl (amide) compounds of the present invention.

Referring back now to the reaction between the reagent of Formula 2 with an amine compound of Formula 3 it is noted that the amine compounds are, generally speaking, available in accordance with the state-of-the-art. as described in the scientific and patent literature. More specifically, the amine compounds of Formula 3 can be prepared as described in the scientific and patent literature, or from known compounds of the literature, by such chemical reactions or transformations which are within the skill of the practicing organic chemist. Reaction Scheme 6 illustrates examples for the preparation of amine compounds of Formula 3 (where Y is phenyl) from commercially available starting materials (Aldrich Chemical Company, or Research Plus, Inc. The illustrated compounds of Formula 3 are used for the synthesis of several preferred compounds of the invention.

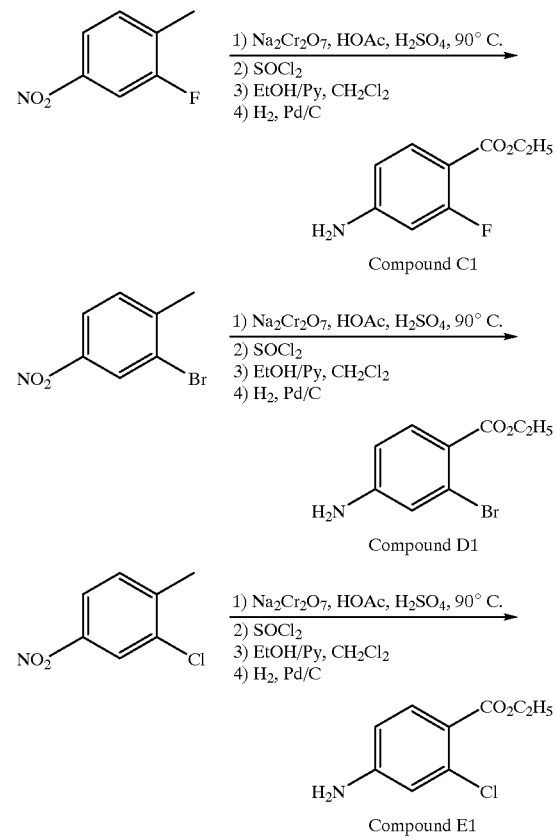

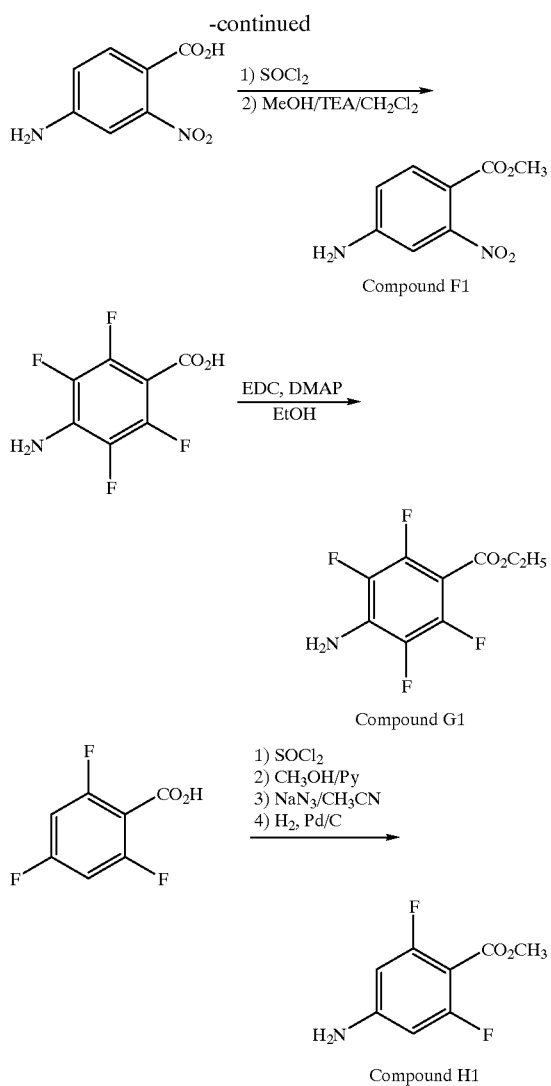

Compound F1

Compound G1

Compound H1

Thus, in accordance with Reaction Scheme 6, 3-nitro-6-methyl-fluorobenzene (Aldrich) is subjected to oxidation, conversion of the resulting carboxylic acid to an acid chloride and thereafter to an ethyl ester, followed by reduction of the nitro group, to yield ethyl 2-fluoro-4-amino-benzoate (Compound $C_1$)- 3-Nitro-6-methyl-bromobenzene (Aldrich) and 3-nitro-6-methyl-chlorobenzene (Aldrich) are subjected to essentially to the same series of reactions to yield ethyl 2-bromo-4-amino-benzoate (Compound $D_1$) and ethyl 2-chloro-4-amino-benzoate (Compound $E_1$), respectively. 2-Nitro-4-aminobenzoic acid (Research Plus) is converted to its methyl ester (Compound $F_1$) through the corresponding acid chloride. 2,3,5,6-Tetrafluoro-4-amino-benzoic acid (Aldrich) is esterified by treatment with ethanol in the presence of 1-(3-dimethylaminopropyl)-3-ethylcarbodiimide hydrochloride (EDC) and 4-dimethylaminopyridine in $CH_2Cl_2$ to give ethyl 2,3,5,6-tetrafluoro-4-amino-benzoate (Compound $G_1$). 2,4,6-Trifluorobenzoic acid (Aldrich) is converted to the methyl ester through the acid chloride, and the 4-fluoro atom is displaced by reaction with sodium azide, followed by hydrogenation, to yield methyl 2,6-difluoro-4-amino benzoate (Compound $H_1$). Compounds $C_1$, $D_1$, $E_1$, $F_1$, $G_1$ and $H_1$ serve as amine reagents in accordance with Formula 3. Further examples of reagents in accordance with Formula 3 are nitro, fluoro, chloro, bromo and trifluoromethyl derivatives of amino substituted heteroaryl carboxylic acids, or their lower alkyl esters, such as ethyl 2-amino-4-chloropyridine 2-carboxylate, ethyl 5-amino-3-chloropyridine 5-carboxylate, and 3,4-dibromo-5-aminothiophene-2-carboxylic acid. The latter examples can be prepared by respective chlorination or bromination of 2-aminopyridine-5-carboxylic acid or of its ester, 3-aminopyridine-6-carboxylic acid or of its ester (described in WO 93/06086) and of 2-aminothiophene-5-carboxylic acid (described in PCT/US92/06485).

The reaction between the compounds of Formula 2 and Formula 3 or between compounds of Formula 2a and 3a, described above, comprises the actual synthesis of the carbamoyl (amide) compounds of the invention. Numerous examples of this reaction are described in detail in the experimental section below. The carbamoyl (amide) compounds of the invention can be converted into thiocarbamoyl (thioamide) compounds of the invention where with reference to Formula 1 Z is S, by reacting the carbamoyl (amide) compound with 2,4-bis(4-methoxyphenyl)-1,3-dithia-2,4-diphosphetane-2,4-disulfide (Lawesson's reagent). This reaction is illustrated in Reaction Scheme 7 for two specific examples for the compounds of the invention.

Reaction Scheme 7

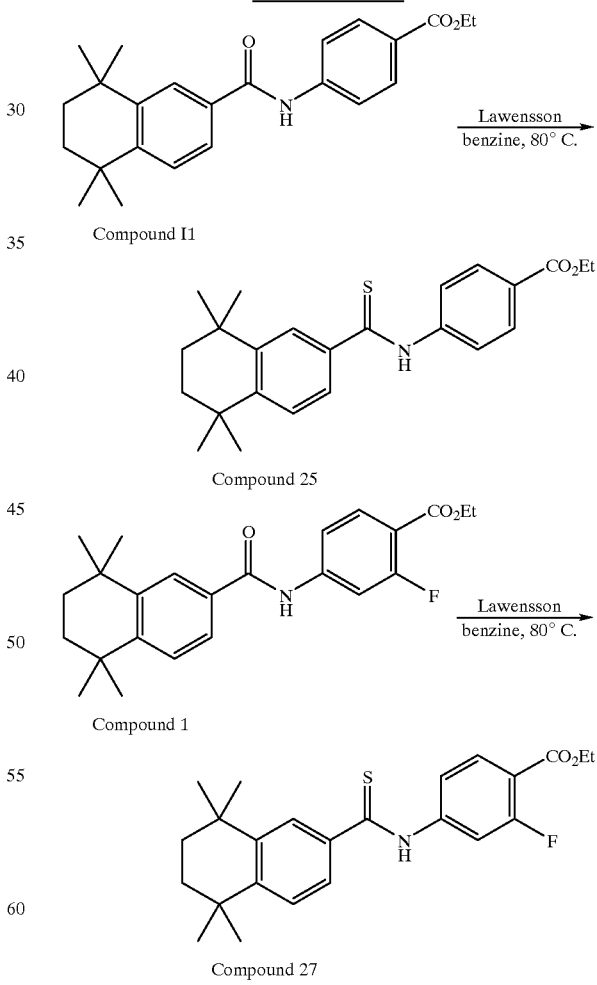

Compound I1

Compound 25

Compound 1

Compound 27

In Reaction Scheme 7 one starting material ethyl 4-[5', 6',7',8'-tetrahydro-5',5',$_8$1,8'- tetramethylnaphthalen-2-yl) carbamoyl]benzoate (Compound $I_1$) is obtained in accordance with the teachings of Kagechika et al. J. Med Chem. 1988 31, 2182–2192. The other starting material, ethyl 2-fluoro-4-[5',6',7',8'-tetrahydro-5',5',8',8'-tetramethylnaphthalen-2-yl)carbamoyl]benzoate (Compound 1) is obtained in accordance with the present invention.

Reaction Scheme 8

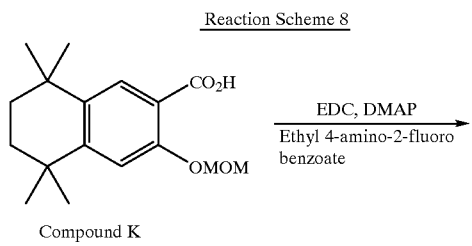

Compound K

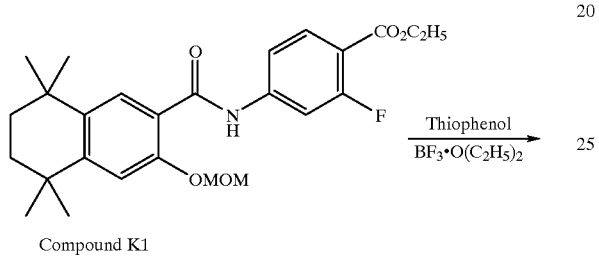

Compound K1

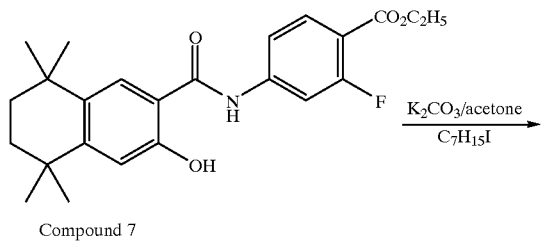

Compound 7

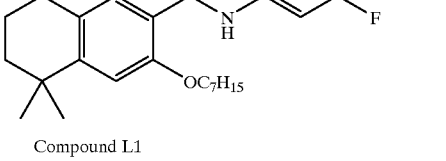

Compound L1

Reaction Scheme 9

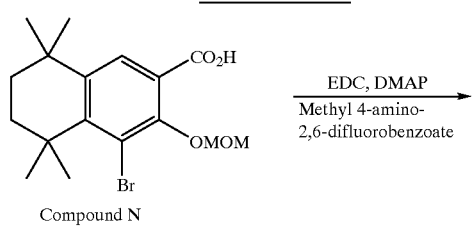

Compound N

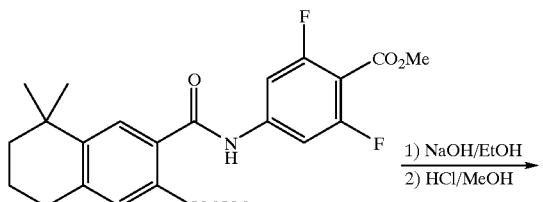

Compound M1

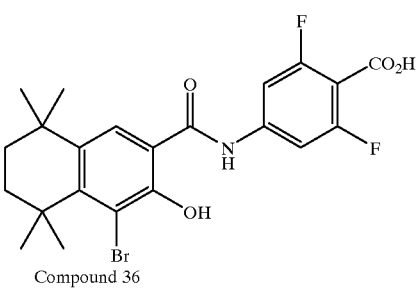

Compound 36

Reaction Scheme 10

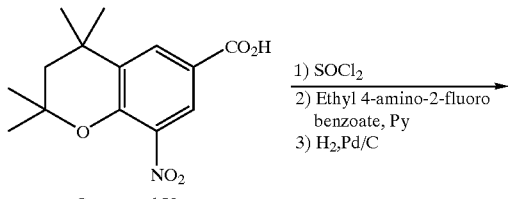

Compound V

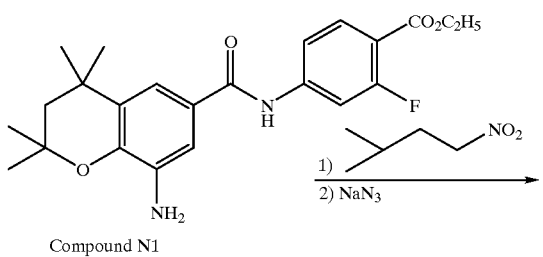

Compound N1

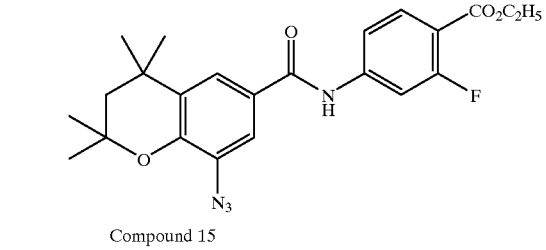

Compound 15

Reaction Scheme 10

Reaction Schemes 8, 9 and 10 disclose examples for the preparation of carbamoyl (amide) compounds of the invention, first by a coupling reaction of a compound of Formula 2 with a compound of Formula 3, followed by one or more reactions performed on the carbamoyl (amide) compound that has been first obtained directly in the coupling reaction. Thus, as is shown in Reaction Scheme 8, 5,6,7,8-tetrahydro-5,5,8,8-tetramethyl-3-methoxymethoxynaphthalene-2-carboxylic acid (Compound K) is coupled with ethyl 4-amino-2-fluorobenzoate (Compound $C_1$) in $CH_2Cl_2$ in the presence of 1-(3-dimethylaminopropyl)-3-ethylcarbodiimide hydrochloride (EDC) and dimethylaminopyridine (DMAP) to give ethyl 2-fluoro-4-[5',6',7',8'-tetrahydro-5',5',8',8'-tetramethyl-2'-methoxymethoxy-naphthalen-3'-yl)carbamoyl]benzoate (Compound $K_1$). The methoxymethyl protecting group is removed from Compound $K_1$ by treatment with thiophenol and borontrifluoride ethereate resulting in ethyl 2-fluoro-4-[5',6',7',8'-tetrahydro-5',5',8',8'-tetramethyl-2'-hydroxy-naphthalen-3'-yl)carbamoyl]-benzoate (Compound 7). The hydroxy function of Compound 7 is converted into an n-hexyl ether by treatment with hexyl iodide in the presence of mild base.

In accordance with Reaction Scheme 9 5,6,7,8-tetrahydro-5,5,8,8-tetramethyl-1-bromo-2-methoxymethoxynaphthalene-3-carboxylic acid (Compound N) is coupled with methyl 4-amino-2,6-difluorobenzoate (Compound $H_1$) in $CH_2Cl_2$ solvent in the presence of ethylcarbodiimide hydrochloride (EDC) and DMAP to provide methyl 2,6-difluoro-4-[(5',6',7',8'-tetrahydro-5',5',8',8'-tetramethyl-1'-bromo-2'-methoxymethoxy- naphthalen-3'-yl)carbamoyl]benzoate (Compound $M_1$), from which the esterifying methyl group and the methoxymethyl protecting group are removed by treatement with base and acid, respectively.

Reaction Scheme 10 discloses the example of converting 2,2,4,4-tetramethyl-8-nitrochroman-6-carboxylic acid (Compound V) into the corresponding acid chloride by treatment with thionyl chloride, followed by coupling with ethyl 4-amino-2-fluorobenzoate (Compound Cl) and hydrogenation to yield ethyl 2-fluoro-4-[(2',2',4',4'-tetramethyl-8'-amino-6'-chromanyl)carbamoyl]benzoate (Compound $N_1$). Compound $N_1$ is converted to the corresponding 8-azido compound, ethyl 2-fluoro-4-[(2',2',4',4'-tetramethyl-8'-azido-6'-chromanyl)carbamoyl]benzoate (Compound 15) by treatment of isoamyl nitrate and $NaN_3$.

Reaction Scheme 11

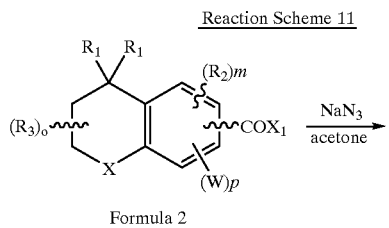

Formula 2

Formula 6

↓ t-BuOH

Formula 7

↓ $H_2O$

Formula 2a

Reaction Scheme 11 illustrates the synthesis of the primary amine compounds of Formula 2a from the acid chlorides ($X_1$=Cl) or other form of activated acids of Formula 2 where the primary amine of Formula 2a is not available by a published literature procedure. Thus, substantially in accordance with the step of a Curtius rearrangement, the acid chloride of Formula 2 is reacted with sodium azide in acetone to yield the azide compound of Formula 6. The azide of Formula 6 is heated in a polar high boiling solvent, such as t- butanol, to provide the intermediate isocyanate of Formula 7, which is hydrolyzed to yield a compound of Formula 2a.

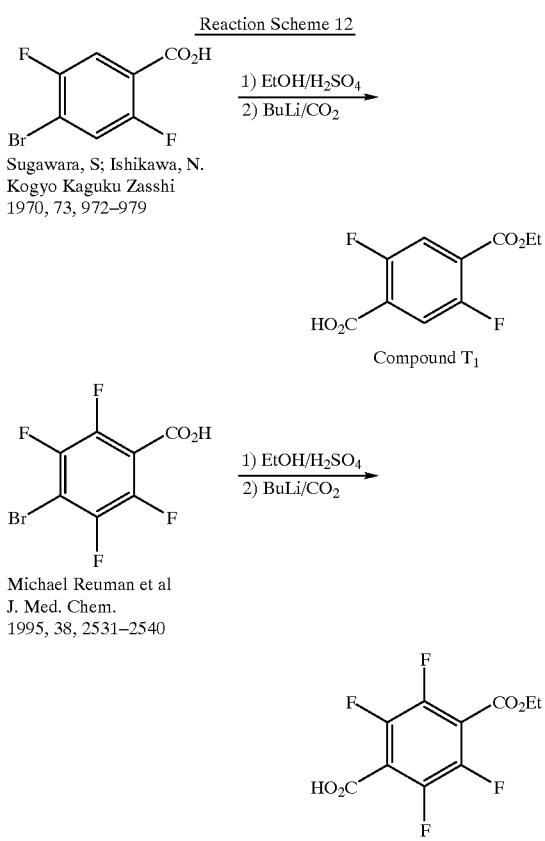

Reaction Scheme 12

Sugawara, S; Ishikawa, N.
Kogyo Kaguku Zasshi
1970, 73, 972–979

Compound $T_1$

Michael Reuman et al
J. Med. Chem.
1995, 38, 2531–2540

Reaction Scheme 12 illustrates examples for preparing compounds of Formula 3a where such compounds are not available commercially or by a published literature procedure. Thus, by way of example 2,5-difluoro-4-bromobenzoic acid (available by the literature procedure of Sugawara et al. Kogyo Kaguku Zasshi 1970, 73, 972–979) is first esterified by treatment with ethyl alcohol and acid to yield the corresponding ester, and thereafter is reacted with butyl lithium followed by carbon dioxide to give the monoester of 2,5-difluoro terephthalic acid (Compound $T_1$). A similar sequence of reactions performed on 2,3,5,6-difluoro-4-bromobenzoic acid (available by the literature procedure of Reuman et al. J. Med. Chem. 1995, 38, 2531–2540) yields the monoester of 2,3,5,6-tetrafluoroterephthalic acid. The just illustrated sequence of reaction can be, generally speaking, utilized for the synthesis of all compounds of Formula A 3a with such modification which will become readily apparent to those skilled in the art, where such compounds are not available by a known literature procedure.

Numerous other reactions suitable for preparing compounds of the invention, and for converting compounds of Formula 1 within the scope of the present invention into still further compounds of the invention, and also for preparing the reagents of Formula 2, Formula 3, Formula 2a and Formula 3a will become readily apparent to those skilled in the art in light of the present disclosure. In this regard the following general synthetic methodology, applicable for conversion of the compounds of Formula 1 into further homologs and/or derivatives, and also for preparing the reagents of Formula 2 and 3, (as well as 2a and 3a) is noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

A means for making compounds where A is $(CH_2)_q$ (q is 1–5) is to subject the compounds of Formula 1, where B is an acid or other function, to homologation, using the well known Arndt-Eistert method of homologation, or other known homologation procedures. Similar homologations (and several of the other herein mentioned synthetic transformations) can be transformed on the reagent of Formula 3. Compounds of the invention, where A is an alkenyl group having one or more double bonds can be made, for example, by having the requisite number of double bonds incorporated into the reagent of Formula 3. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of the invention where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropyl amide.

The acids and salts derived from compounds of Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium or lithium hydroxide. The solution is stirred for an extended period of time, between 15 and 20 hours, cooled, acidified and the hydrolysate recovered by conventional means.

The amide (in Formula 1 B is $CONR_9R_{10}$) may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/ oxalyl chloride in methylene chloride (Omura, K., Swern, D., *Tetrahedron.* 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 1 where B is H can be prepared from the corresponding halogenated aromatic compounds, preferably where the halogen is I.

SPECIFIC EXAMPLES

Ethyl 4-Amino-2-fluorobenzoate (Compound $C_1$)

To a mixture of 2-fluoro-4-nitrotoluene (1.0 g, 6.4 mmol, Aldrich) and $Na_2Cr_2O_7$ (2.74 g, 8.4 mmol) in 13.7 ml of HOAc was added slowly 6.83 ml of $H_2SO_4$. This mixture was slowly heated to 90° C. for 1 h to give a greenish heterogeneous solution. The mixture was cooled to room temperature and diluted with ethyl acetate. The PH of the solution was adjusted to 4 with NaOH (aq.). The mixture was extracted with more ethyl acetate. The organic layer was washed with $NaHCO_3$ (sat.), then brine and dried over $Na_2SO_4$. After filtration, the solution was concentrated to dryness which then was dissolved in 6 ml of $SOCl_2$, and heated at 80° C. for 1 h. The excess of $SOCl_2$ was removed under reduced pressure and the residue was dissolved in 5 ml of $CH_2Cl_2$, 2 ml of EtOH and 2 ml of pyridine. The mixture was stirred at room temperature for 2 h and concentrated to dryness. Ethyl 2-fluoro-4-nitrobenzoate was obtained as a white solid after column chromatography of the residue with ethyl acetate/hexane (1/9). This solid was then dissolved in 10 ml of ethyl acetate, and Pd/C (50 mg) was added. Hydrogenation with a hydrogen balloon converted ethyl 2-fluoro-4-nitrobenzoate into the title compound.

$^1$H NMR δ 7.77 (t, J=8.4 Hz, 1H), 6.41 (dd, $J_1$=8.6, $J_2$=2.2 Hz, 1H), 6.33 (dd, $J_1$=13.0, $J_2$=2.2 Hz, 1H), 4.33 (q, J=7.1 Hz, 2H), 4.3 (b, 2H), 1.37 (t, J=7.1 Hz, 3H).

Methyl 4-Amino-2,6-difluorobenzoate (Compound $H_1$)

A solution of trifluorobenzoic acid (150 mg, 0.85 mmol, Aldrich) in 0.5 ml of $SOCl_2$ was heated under reflux for 2h. The reaction mixture was cooled to room temperature, and excess of $SOCl_2$ was removed under reduced pressure. The residue was dissolved in 1 ml of pyridine and 0.2 ml of methanol. After stirring at room temperature for 30 min, solvent was removed and the residue was purified by column chromatography (ethyl acetate/hexane 1/10) to give methyl trifluoro- benzoate as a colorless oil. This oil was then dissolved in 1 ml of $CH_3CN$, then a solution of $NaN_3$ (100 mg, 1.54 mmol) in 0.5 ml of water was added. The reaction mixture was refluxed for two days. Salt was filtered and the remaining solution was concentrated to an oil. This oil was then dissolved in 1 ml of methanol, followed by a catalytic amount of Pd/C (10%, w/w). The reaction mixture was hydrogenated under a hydrogen balloon for 12 h. Catalyst was removed and the solution was concentrated to an oil. After column chromatography (ethyl acetate/hexane 1/3), the title product was obtained as colorless crystals.

$^1$H NMR δ 6.17 (d, J=10.44 Hz, 2H), 4.2 (b, 2H), 3.87 (s, 3H).

8-Bromo-2,2,4,4-tetramethyl-6-chromanoic acid (Compound P)

To a solution of 2,2,4,4-tetramethyl-6-chromanoic acid (200 mg, 0.85 mmol) in 0.5 ml of AcOH was added $Br_2$ (0.07 ml, 1.28 mmol). The resulting dark-orange solution was stirred at room temperature for overnight. The excess bromine was removed under reduced pressure. Then the solution was poured into 5 ml of water and extracted with ethyl acetate (3×3 ml). The combined ethyl acetate layers were further washed with $NaHCO_3$ (sat.), brine and dried over $MgSO_4$. After concentration, the residue was purified by column chromatography (silica gel, ethyl acetate/hexane 1/3) to yield the desired product (170 mg, as white solids.

$^1$H NMR δ 8.11 (d, J=2.2 Hz, 1H), 8.00 (d, J=2.2 Hz, 1H), 1.90 (s, 2H), 1.43 (s, 6H), 1.39 (s, 6H).

8-Iodo-2,2,4,4-tetramethyl-6-chromanoic Acid (Compound X)

To a solution of 2,2,4,4-tetramethyl-6-chromanoic acid (66 mg, 0.28 mmol) in 0.8 ml of AcOH was added ICl (0.07 ml, 1.4 mmol). The resulting colored solution was stirred at room temperature for overnight. Following the same procedure as for the synthesis of 8-bromo- 2,2,4,4-tetramethyl-6-chromanoic acid (Compound P), the reaction gave the title compound (107 mg) as white solids.

$^1$H NMR δ 8.35 (d, J=2.2 Hz, 1H), 8.03 (d, J=2.2 Hz, 1H), 1.87 (s, 2H), 1.43 (s, 6H), 1.38 (s, 6H).

2,2,4,4-Tetramethyl-8-trifluoromethylchroman-6-oic acid (Compound S)

A solution of 8-bromo-2,2,4,4-tetramethyl-6-chromanoic acid (Compound R, 150 mg, 0.48 mmol) in 1 ml of $SOCl_2$ was refluxed for 2 h. After cooling to room temperature, the excess of $SOCl_2$ was removed under reduced pressure and the residue was dissolved in 1 ml of pyridine and 0.2 ml of methanol. The mixture was stirred at room temperature for 30 min. Solvent was removed and the residue was passed through a column (silica gel, ethyl acetate/hexane 1/10) to give the methyl 8-bromo-2,2,4,4-tetramethylchromanoate (158 mg) as a colorless oil. To a solution of this methyl ester in 3 ml of N-methylpyrrolidone (NMP) was added $NaCO_2CF_3$ (502 mg, 3.7 mmol) and CuI (350 mg, 1.84 mmol). The resulting mixture was heated to 175° C. (bath temp) for 2 h. The resulting mixture was cooled to room temperature and poured into ice-water. The product was extracted into ethyl acetate (3×3 ml). The combined organic layers were dried and concentrated to dryness. The crude material was purified by column chromatography (ethyl acetate/chloroform 1/10) to give the title compound as a colorless oil (120 mg). This was hydrolyzed under standard conditions to give the title compound.

$^1$H NMR δ 8.21 (d, J=2.1 Hz, 1H), 8.17 (d, J=2.1 Hz, 1H), 1.92 (s, 2H), 1.41 (s, 12H).

Ethyl 8-Nitro-2,2,4,4-tetramethyl-6-chromanoate (Compound W)

Ethyl 2,2,4,4-tetramethyl-6-chromanoate (150 mg, 0.57 mmol) was slowly added to 0.3 ml of conc. $H_2SO_4$ at 0° C. To this mixture was added very slowly 0.03 ml of $HNO_3$. The reaction mixture was stirred at 0° C. for 30 min and poured into ice-water. The product was extracted into 5 ml of ethyl acetate, washed with $NaHCO_3$ (sat.), brine and dried over $MgSO_4$. After concentration, the product was purified by column chromatography (ethyl acetate/hexane 1/10) to yield 74 mg of light-yellow oil.

$^1$H NMR δ 8.24 (d, J=2.1 Hz, 1H), 8.17 (d, J=2.1 Hz, 1H), 4.38 (q, J=7.1 Hz, 2H), 1.95 (s, 2H), 1.43 (s, 6H), 1.42 (s, 6H), 1.40 (t, J=7.1 Hz, 3H).

2-Oxo-4,4,8-trimethylchroman (Compound $P_1$)

In a 500 ml of round bottom flask, NaH (1.66 g, 60% suspension in oil, 0.046 mol) was washed with dry hexane. Then, dry THF (22 ml) was added followed by o- cresol (5 g, 0.046 mol) in 10 ml of dry THF. The reaction mixture was stirred at 0° C. for 30 min followed by addition of 3,3-dimethyl acryloyl chloride in 10 ml of THF. The resulting white slurry was stirred at room temperature for 12 h, then slowly quenched with water. The mixture was then extracted with ethyl acetate. The organic layer was washed with brine, water and dried over $MgSO_4$. After filtration and removal of the solvent, a yellow oil was obtained (10.44 g). This oil was then dissolved in 50 ml of dry $CH_2Cl_2$, and was canulated into a solution of $AlCl_3$ (10.8 g, 0.069 mmol) in 10 ml of $CH_2Cl_2$. The reaction mixture was stirred at room temperature for 12 h. Then ice-water was carefully added and the organic layer was separated, and washed with $NaHCO_3$ (sat), brine, water and finally dried over $MgSO_4$ After removal of the drying agent and solvent, the residue was purified by column chromatography (silica gel, ethyl acetate/hexane 1/9) to yield the title compound (4.408 g) as an oil.

$^1$H NMR δ 7.1 (m, 3H), 2.62 (s, 2H), 2.33 (s, 3H), 1.36 (s, 6H).

2,4-Dimethyl-4-(2'-hydroxy-3'-methylphenyl)pentan-2-ol (Compound $R_1$)

To a solution of 2-oxo-4,4,8-trimethylchroman (Compound $P_1$, 2.20 g, 11.5 mmol) in 40 ml of dry ethyl ether was added methyl magnesium bromide (12.67 ml, 38 mmol, 3 M solution in THF). The reaction mixture was stirred at room temperature for 12 h, then quenched with $NH_4Cl$ (sat.) until all precipitate dissolved. The mixture was extracted with diethyl ether and the combined organic layers were separated and washed with brine, water and dried over $MgSO_4$. After filtration and removal of the solvent, the title compound was obtained as a tan solid (2.215 g).

$^1$H NMR δ 7.16 (d, J=7.88 Hz, 1H), 7.00 (d, J=6.72 Hz, 1H), 6.81 (t, J=7.6 Hz, 1H), 5.89 (b, 1H), 2.21 (s, 3H), 2.17 (s, 2H), 1.48 (s, 6H), 1.10 (s, 6H).

2,2,4,4,8-Pentamethyl-6-bromochroman (Compound Z)

A solution of 2,4-dimethyl-4-(2'-hydroxy-3'-methylphenyl)pentan-2-ol (Compound $R_1$, 2.215 g, 9.98 mmol) in 30 ml of 15% of $H_2SO_4$ was heated to 110° C. After cooling to room temperature, the reaction mixture was extracted with diethyl ether. The organic layer was washed with $NaHCO_3$ (sat.), brine and water. After filtration and removal of solvent, the residue was passed through a column (silica gel, pure hexane) to give the title compound as a clear oil (1.636 g). This oil was then dissolved in 1.5 ml of HOAC, then $Br_2$ (0.4113 ml, 7.98 mmol) was added. The reaction mixture was stirred at room temperature for 12 h. Solvent was removed under reduced pressure and to the residue was added ethyl acetate, and the resulting mixture was washed with $NaHCO_3$(sat.), brine, water and dried over $MgSO_4$. After filtration and removal of solvent, the residue was passed through a column (silica gel, pure hexane) to give the title compound as a white solid (2.227 g).

$^1$H NMR δ 7.21 (s, 1H), 7.06 (s, 1H), 2.14 (s, 3H), 1.79 (s, 2H), 1.32 (s, 6H), 1.31 (s, 6H).

2,2,4,4,8-Pentamethyl-6-chromanoic Acid (Compound $A_1$)

To a solution of 2,2,4,4, 8-pentamethyl-6-bromo- chroman (Compound Z) (1.2 g, 4.24 mmol) in 18 ml of dry THF at −78° C. under argon gas was added slowly 5.48 ml of t-BuLi (1.7 M in hexane, 9.33 mmol). The reaction mixture was stirred at −78° C. for 1 h. Then $CO_2$ was bubbled through the solution for 1 h. After removal of $CO_2$ stream, the reaction mixture was stirred for an additional hour at −78° C. Then 10% of HCl was added. After warming up to room temperature, the reaction mixture was extracted with ethyl acetate. The organic layer was further washed with brine and dried over $Na_2SO_4$. After concentration, the residue was purified by column chromatography (ethyl acetate/hexane 5/95) to yield the title compound as a white solid (774 mg).

$^1$H NMR δ 7.96 (s, 1H), 7.75 (s, 1H), 2.23 (s, 3H), 1.88 (s, 2H), 1.39 (s, 6H).

8-Bromo-4,4-dimethyl-6-chromanoic Acid (Compound $B_1$)

Using the same procedure as for the synthesis of 8-bromo-2,2,4,4-tetramethylchromanoic acid (Compound P) but using 4,4-dimethylchromanoic acid (100 mg, 0.49 mmol), the title compound was obtained as a white solid.

$^1$H NMR δ 8.10 (d, J=2.1 Hz, 1H), 7.98 (d, J=2.1 Hz, 1H), 4.39 (t, J=5.44 Hz, 2H), 1.89 (t, J=5.4 Hz, 1H), 1.38 (s, 6H).

Ethyl 2-Amino-1-bromo-5,5,8,8-tetrahydro-5,5,8,8-tetramethylnaphthalene-3-carboxylate (Compound D)

To a solution of ethyl 5,6,7,8-tetrahydro-5,5,8,8-tetramethyl-3-aminonaphthalene-2-carboxylate (Compound C, 58 mg, 0.21 mmol) in 2 ml of HOAC was added $Br_2$ (0.02 ml, 0.42 mmol). The orange solution was stirred at room temperature for 2 days. The excess $Br_2$ and HOAC were removed under reduced pressure and the residue was passed through a column (silica gel, ethyl acetate/hexane 1/10) to yield the title compound as a light-orange oil (59 mg, 79.5%).

$^1$H NMR δ 7.90 (s, 1H), 6.41 (b, 2H), 4.36 (q, J=7.2 Hz, 2H), 1.70 (m, 4H), 1.58 (s, 6H), 1.40 (t, J=7.2 Hz, 3H), 1.28 (s, 6H).

Ethyl 5,6,7,8-tetrahydro-5,5,8,8-tetramethyl-4-bromonaphthalene-2-carboxylate (Compound E)

Ethyl 2-Amino-1-bromo-5,5,8,8-tetrahydro-5,5,8,8-tetramethylnaphthalene-3-carboxylate (Compound D, 59 mg, 0.17 mmol) was dissolved in 2 ml of EtOH at 0° C. To this solution was added 1 ml of trifluoroacetic acid and 1 ml of isoamylnitrite. The reaction mixture was stirred at 0° C. for 30 min then $H_3PO_2$ (0.325 ml, 3.14 mmol) was added. The reaction mixture was allowed to warm to room temperature and stirred for 12 h. $NaHCO_3$ (sat.) was added and the reaction mixture was extracted with ethyl acetate, dried over $MgSO_{41}$ filtered and concentrated to give an oil. The product was purified by column chromatography (silica gel, ethyl acetate/hexane 1/10) to give the title compound as a colorless oil.

$^1$H NMR δ 8.02 (d, J=2.0 Hz, 1H), 7.95 (d, J=2.0 Hz, 1H), 4.35 (q, J=7.1 Hz, 2H), 1.71 (m, 4H), 1.56 (s, 6H), 1.38 (t, J=7.1 Hz, 3H), 1.31 (s, 6H).

Ethyl 5,6,7,8-tetrahydro-5,5,8,8-tetramethyl-3-fluoronaphthalen-2-yl-carboxylate (Compound G)

In an ice bath, ethyl 5,6,7,8-tetrahydro-5,5,8,8-tetramethyl-3-aminonaphthalene-2-carboxylate (Compound C, 150 mg, 0.55 mmol) was added 0.24 ml of $HBF_4$ (48% solution in water), followed by a solution of $NaNO_2$ (81 mg, 1.16 mmol) in 1 ml of water. The slurry was left in a refrigerator for 3 days. The reaction mixture was washed successively with ethyl acetate until TLC showed no UV visible spot at the baseline. The ethyl acetate layer was dried with $MgSO_4$ and the solution was concentrated to an oil. The oil was further dissolved in 1 ml of toluene and the mixture was heated under reflux for 2 h. After the reaction cooled to room temperature, solvent was evaporated and the residue was passed through a column (silica gel, ethyl acetate/hexane 1/10) to give the title compound as an oil.

$^1$H NMR δ 7.85 (d, J=7.8 Hz, 1H), 7.04 (d, J=12.3 Hz, 1H), 4.38 (q, J=7.1 Hz, 2H), 1.69 (s, 4H), 1.38 (t, J=7.1 Hz, 3H), 1.30 (s, 6H), 1.28 (s, 6H).

2-Bromo-3-hydroxy-5,5,8,8-tetrahydro-5,5,8,8-tetramethylnaphthalene (Compound I)

Using the same procedure as for the synthesis of 8-bromo-2,2,4,4-tetramethyl-6-chromanoic acid (Compound P) but using 2-hydroxy-5,5,8,8-tetrahydro-5,5,8,8-tetramethyltetralin (700 mg, 3.43 mmol) and $Br_2$ (0.177 ml, 3.43 mmol) in 1.5 ml of HOAC, the title compound was obtained as a white solid (747 mg).

¹H NMR δ 7.36 (s, 1H), 6.96 (s, 2H), 5.32 (b, 1H), 1.66 (s, 4H), 1.25 (s, 12H).

5,6,7,8-Tetrahydro-5,5,8,8-tetramethyl-3-methoxymethoxy-2-bromonaphthalene (Compound J)

To a solution of 2-bromo-3-hydroxy-5,5,8,8-tetrahydro-5,5,8,8-tetramethylnaphthalene (Compound I, 600 mg, 2.12 mmol) and catalytic amount of Bu₄NBr in 20 ml of dry CH₂Cl₂ at 0° C. was added diisoproylethylamine (1.138 ml, 12.75 mmol), followed by methoxymethyl chloride (0.484 ml, 6.39 mmol). The reaction mixture was heated at 45° C. for 12 h. The reaction mixture was washed with 10% of citric acid, then NaHCO₃ (sat.), brine and dried over MgSO₄. After filtration and removal of the solvent, the residue was purified by column chromatography (ethyl acetate/hexane 1/9) to yield the title compound (722 mg) as a white solid.

¹H NMR δ 7.43 (s, 1H), 7.06 (s, 1H), 5.21 (s, 2H), 3.54 (s, 3H), 1.66.(s, 4H), 1.26 (s, 6H), 1.25 (s, 6H).

3-Methoxymethoxy-5,5,8,8-tetramethyl-5,6,7,8-tetrahydronaphthalen-2-yl carboxylic acid (Compound K)

Using the same procedure as for the synthesis of 2,2,4,4,8-pentamethyl-6-chromanoic acid (Compound A₁) but using 5,6,7,8-tetrahydro-5,5,8,8-tetramethyl-3-methoxymethoxy-2-bromonaphthalene (Compound J, 722 mg, 2.21 mmol) and 2.86 ml of t-BuLi (4.87 mmol, 1.7 M solution in hexane), the title compound was obtained as a white solid (143 mg).

¹H NMR δ 8.12 (s, 1H), 7.19 (s, 1H), 5.40 (s, 2H), 3.58 (s, 3H), 1.70 (s, 4H), 1.30 (s, 12H).

Ethyl 2-Fluoro-4-[(5',6',7',8'-tetrahydro-5',5',8',8'-tetramethylnaphthalen-2'-yl)carbamoyl]benzoate (Compound 1)

To 5,5,8,8-tetramethyl-5,6,7,8-tetrahydro-2-naphthoic acid (46 mg, 0.2 mmol) was added 1 ml thionyl chloride. This mixture was refluxed for 2 h. Excess thionyl chloride was removed under reduced pressure and the residue was dissolved in 2 ml of CH₂Cl₂. To this solution was added ethyl 4-amino-2-fluorobenzoate ((Compound C₁, 37 mg, 0.2 mmol) followed by 0.5 ml of pyridine. The reaction mixture was stirred at room temperature for 4 h and was concentrated under reduced pressure. The residue was purified by column chromatography (ethyl acetate/hexane 1/10) to give the title compound as white solids.

¹H NMR δ 8.06 (b, 1H), 7.93 (t, J=8.4 Hz, 1H), 7.85 (d, J=2.0 Hz, 1H), 7.78 (dd, J₁ =2.0 Hz, J₂=12.9 Hz, 1H), 7.55 (dd, J₁=2.0 Hz, J₂=8.2 Hz, 1H), 7.40 (d, J=8.3 Hz, 1H), 7.32 (dd, J₁=2.02 Hz, J₂=8.8 Hz, 1H), 4.38 (q, J=7.2 Hz, 2H), 1.71 (s, 4H), 1.40 (t, J=7.2 Hz), 1.32 (s, 6H), 1.30 (s, 6H).

Ethyl 4-[(3'-fluoro-5',6',7',8'-tetrahydro-5',5',8',8'-tetramethylnaphthalen-2'-yl)carbamoyl]benzoate (Compound 3)

Ethyl 5,6,7,8-tetrahydro-5,5,8,8-tetramethyl-3-fluoronaphthalene-2-carboxylate (Compound G, 75 mg, 0.27 mmol) was dissolved in a mixture of 3 ml of EtOH and 1 ml of NaOH (1 M in water). The reaction mixture was left overnight at room temperature. The reaction was neutralized with 5% of HCl. Water (2 ml) was added and the mixture was extracted with ethyl acetate (3×3 ml). The combined layers were washed once with 3 ml of brine and dried over MgSO₄. After filtration, the clear organic solution was concentrated to give 3-fluoro-5,5,8,8-tetrahydro-5,5,8,8-methylnaphthalen-2-yl carboxylic acid. Using the same procedure as for ethyl 2-fluoro-4-[(5',6',7',8'-tetrahydro-5',5',8',8'-tetra- methylnaphthalen-2'-yl)carbamoyl]benzoate (Compound 1), except using ethyl 4-amino benzoate (45 mg, 0.27 mmol), the carboxylic acid was converted to the title compound (white solid).

¹H NMR δ 8.66 (b, 1H), 8.13 (d, J=7.8 Hz, 1H), 8.05 (d, J=8.3 Hz, 2H), 7.76 (d, J=8.3 Hz, 2H), 7.07 (d, J=12.3 Hz, 1H), 4.36 (q, J=7.1 Hz, 2H), 1.70 (s, 4H), 1.49 (t, J=7.1 Hz, 3H), 1,32 (s, 6H), 1.30 (s, 6H).

Ethyl 2-Fluoro-4-[(5',6',7',8'-tetrahydro-4'-bromo- 5',5',8',8'-tetramethylnarphthalen-2'- yl)carbamoyl]benzoate (Compound 5)

Using the same procedure as for the synthesis of ethyl 2-fluoro-4-[-5',6',7',8'-tetrahydro-5',5',8',8'-tetramethylnaphthalen-2'-yl)carbamoyl]benzoate (Compound 1), but using 5,6,7,8-tetrahydro-5,5,8,8-tetramethyl-4-bromonaphthalene-2-carboxylic acid (Compound P), the title compound was obtained as a white solid.

¹H NMR δ 8.30 (b, 1H), 7.92 (t, J=8.4 Hz, 1H), 7.84 (d, J=2.1 Hz, 1H), 7.81 (d, J=2.1 Hz, 1H), 7.74 (dd, J₁=2.1 Hz, J₂=12.8 Hz, 1H), 7.35 (dd, J₁=2.0 Hz, J₂=8.4 Hz, 1H), 4.36 (q, J=7.2 Hz, 2H), 1.67 (m, 4H), 1.55 (s, 6H), 1.39 (t, J=7.2 Hz, 3H), 1.31 25 (s, 6H).

Ethyl 2-Fluoro-4-[(3'-methoxymethoxy-5',6',7',8'-tetrahydro-5',5',8',8'-tetramethylnaphthalen-2'-yl) carbamoyl]benzoate (Compound K₁)

Using the same procedure as for the synthesis of ethyl 2-fluoro-4-[(3'-methoxymethoxy-4'-bromo- 5',6',7',8'-tetrahydro-5',5',8',8'- tetramethylnaphthalen-2'-yl) carbamoyl]benzoate (Compound S₁), but using 3-methoxymethoxy-5,5,8,8-tetramethyl- 5,6,7,8-tetrahydronaphthalen-2-yl carboxylic acid (Compound K, 143 mg, 0.49 mmol) and 4-amino-2-fluorobenzoate (Compound C₁ 98.5 mg, 0.54 mmol), the title compound was obtained as a white solid.

¹H NMR δ 10.1 (b, 1H), 8.20 (s, 1H), 7.93 (t, J=8.8 Hz, 1H), 7.83 (d, J=13.4 Hz, 1H), 7.29 (d, J=8.0 Hz, 1H), 5.41 (s, 2H), 4.39 (q, J=7.1 Hz, 2H), 3.59 (s, 3H), 1.70 (s, 4H), 1.31 (s, 12H), 1.26 (t, J=7.1 Hz, 3H).

Ethyl 2-Fluoro-4-[(3'-hydroxy-5',6',7',8'-tetrahydro- 5',5',8',8'-tetramethyl-2-naphthalenyl)carbamoyl]benzoate (Compound 7)

A solution of ethyl 2-fluoro-4-[(3'-methoxymethoxy-5',6',7',8'-tetrahydro-5', 5',8',8'-tetramethyl- naphthalen-2'-yl) carbamoyl]benzoate (Compound K₁, 50.7 mg, 0.11 mmol) in 2 ml of CH₂Cl₂ was added thiophenol (0.061 ml, 0.55 mmol). The reaction mixture was stirred at 0° C. for 5 min, then BF₃.Et₂O (0.027 ml, 0.22 mmol) was added. The reaction mixtrue was stirred at 0 ° C. for 2 h, then NaHCO₃ (sat.) was added. The organic layer was separated, and washed with brine, water and dried over MgSO₄. After filtration and removal of solvent, the residue was passed through a column (silica gel, ethyl acetate/hexane 1/3) to give the title compound as white solid (44.2 mg).

¹H NMR δ 8.61 (b, 1H), 7.94 (t, J=8.42 Hz, 1H), 7.71 (dd, J=10.8, 2.0 Hz, 1H), 7.53 (s, 1H), 7.35 (dd, J=6.4, 2.0 Hz, 1H), 6.96 (s, 1H), 4.39 (q, J=7.1 Hz, 2H), 1.69 (s, 4H), 1.40 (t, J=7.1 Hz, 3H), 1.29 (s, 6H), 1.27 (s, 6H).

Ethyl 2-Fluoro-4-[(4',4'-dimethyl-8'-bromochroman-6'-yl)carbamoyl]benzoate (Compound 9)

In a 10 ml of round bottom flask, 4,4-dimethyl-8-bromo-6-chromanoic acid (Compound B₁, 139 mg, 0.485 mmol) was added SOCl₂ (1 ml, large excess). The resulting solution was heated at 90° C. for 2 h and let cooled to room temperature. The excess of SOCl₂ was evaporated under reduced pressure. The residue was dissolved in CH₂Cl₂ (3 ml). Ethyl 4-amino-2-fluorobenzoate (Compound C₁, 90 mg, 0.49 mmol) was added followed by pyridine (0.5 ml, large excess). The reaction mixture was stirred for overnight and then concentrated to dryness. The residue was purified by column chromatography with ethyl acetate/hexane (1/5) to yield the title compound as a white solid (190 mg).

¹H NMR δ 7.95 (t, J=8.31 Hz, 1H), 7.88 (b, 1H), 7.83 (d, J=2.2 Hz, 1H), 7.80 (d, J=2.2 Hz, 1H), 7.75 (dd, J=12.89, 2.0 Hz, 1H), 7.30 (dd, J=8.55, 2.0 Hz, 1H), 4.37 (m, 5H), 1.89 (t, J=5.49 Hz, 2H), 1.40 (t, J=7.1 Hz, 3H), 1.39 (s, 6H).

Ethyl 2-Fluoro-4-[(2',2',4',4'-tetramethyl-8'-bromochroman-6'-yl)carbamoyl]benzoate (Compound 11)

Using the same procedure as for ethyl 2-fluoro-4-[(4',4'-dimethyl-8'-bromochroman-6'-yl)carbamoyl]benzo- ate (Compound 9), but using 2,2,4,4-tetramethyl-8-bromo-6-chromanoic acid (Compound P, 70 mg, 0.22 mmol) and ethyl 4-amino-2-fluorobenzoate (Compound $C_1$, 38 mg, 0.22 mmol), the title compound was obtained as a white solid (80 mg, 76%).

¹H NMR δ 8.25 (b, 1H), 7.92 (t, J=8.4 Hz, 1H), 7.83 (s, 2H), 7.74 (dd, $J_1$=2.0, $J_2$=13.0 Hz, 1H), 7.34 (dd, $J_1$=2.0, $J_2$=8.7 Hz, 1H), 4.37 (q, J=7.1 Hz, 2H), 1.88 (s, 2H), 1.41 (s, 6H), 1.39 (t, J=7.1 Hz, 3H), 1.37 (s, 6H).

Ethyl 2-Fluoro-4-[(2',2',4',4'-tetramethyl-8'-trifluoromethylchroman-6'-yl)carbamoyl]benzoate (Compound 13)

Using the same procedure as for ethyl 2-fluoro-4-[(4',4'-dimethyl-8'-bromochroman-6'-yl)carbamoyl]benzo- ate (Compound 9), but using 2,2,4,4-tetramethyl-8-trifluoromethyl-6-chromanoic acid (Compound S, 57 mg, 0.19 mmol) and ethyl 4-amino-2-fluorobenzoate (Compound $C_1$, 35 mg, 0.19 mmol), the title compound was obtained as white solids.

¹H NMR δ 8.06 (d, J=2.2 Hz, 1H), 7.99 (b, 1H), 7.95 (t, J=8.55 Hz, 1H), 7.81 (d, J=2.2 Hz, 1H), 7.76 (dd, J=12.8, 2.1 Hz, 1H), 7.33 (dd, J=8.55, 1.9 Hz, 1H), 4.37 (q, J=7.1 Hz, 2H), 1.93 (s, 2H), 1.41 (s, 12H), 1.40 (t, J=7.2 Hz, 3H).

Ethyl 2-Fluoro-4-[(2', 2',4',4'-tetramethyl-8'-aminochroman-6'-yl)carbamoyl]benzoate (Compound $N_1$)

Using 8-nitro-2, 2, 4, 4-tetramethylchroman-6-carboxylic acid (Compound V) and following the same procedure as for the synthesis of ethyl 2-fluoro-4-[(4',4'-dimethyl-8'-bromochroman-61-yl)carbamoyl]benzoate (Compound 9), ethyl 2-fluoro-4-[2',2',4',4'-tetramethyl-8'-nitrochroman-6'-yl)]carbamoylbenzoate was obtained as a white solid. This compound (50 mg, 0.12 mmol) was dissolved in 2 ml of methanol. A catalytic amount of Pd/C was added to the solution and the solution was maintained under $H_2$ atmosphere (hydrogen balloon) for overnight. The catalyst was removed by filtration and the solvent was evaporated to give the title compound as a white solid.

¹H NMR δ 7.93 (t, J=8.43 Hz, 1H), 7.90 (b, 1H), 7.73 (dd, J=12.9, 2.0 Hz, 1H), 7.29 (dd, J=8.43, 1.96 Hz, 1H), 7.23 (d, J=2.14 Hz, 1H), 7.01 (d, J=2.2 Hz, 1H), 4.35 (q, J=7.1 Hz, 2H), 1.88 (s, 2H), 1.39 (s, 6H), 1.38 (t, J=7.1 Hz, 3H), 1.37 (s, 6H).

Ethyl 2-Fluoro-4-[(2',2',4',4'-tetramethyl-8'-azido- chroman-6'-yl)carbamoyl]benzoate (Compound 15)

To a solution of ethyl 2-fluoro-4-[(2',2',4',4'- tetramethyl-8'-aminochroman-6'-yl)carbamoyl]benzoate (Compound $N_1$, 32 mg, 0.077 mmol) in 3 ml of EtOH was added 0.5 ml of trifluoroacetic acid (TFA) and 0.5 ml of isoamylnitrite at 0C. The reaction was stirred for 2 h when a solution of $NaN_3$ (5 mg, ) in 0.2 ml of water was added. The reaction mixture was allowed to warm to room temperature and stirred for overnight. The solvent was removed and the residue was purified by column chromatography (silica gel, ethyl acetate/hexane 1/10) to give the title compound as a colorless oil.

¹H NMR δ 8.0 (b, 1H), 7.94 (t, J=7.8 Hz, 1H), 7.73 (d, J=12.1 Hz, 1H), 7.64 (s, 1H), 7.31 (dd, J=8.5, 2.0 Hz, 1H), 7.21 (d, J=2.0 Hz, 1H), 4.37 (q, J=7.1 Hz, 2H), 1.90 (s, 2H), 1.39 (t, J=7.1 Hz, 3H), 1.45 (s, 6H), 1.40 (s, 6H).

Methyl 2,6-Difluoro-4-[(2',2',4',4'-tetramethyl-8'-trifluoromethylchroman-6'-yl)carbamoyl]benzoate (Compound 17)

Using the same procedure as for ethyl 2-fluoro-4-[(4',4'-dimethyl-8'-bromochroman-6'-yl)carbamoyl)benzo- ate (Compound 9), but using 2,2,4,4-tetramethyl-8-trifluoromethylchromanoic acid (Compound S, 11.2 mg, 0.037 mmol) and methyl 4-amino-2,6-difluorobenzoate (Compound HI, 6.6 mg, 0.035 mmol), the title compound was obtained as white crystals.

¹H NMR δ 8.21 (b, 1H), 8.05 (s, 1H), 7.82 (s, 1H), 7.36 (d, J=10.20 Hz, 1H), 3.93 (s, 3H), 1.92 (s, 2H), 1.40 (s, 12H).

Ethyl 2-Fluoro-4-[(2',2',4',4'-tetramethyl-8'-iodo- chroman-6'-yl carbamoyl]benzoate (Compound 19)

Using the same procedure as for ethyl 2-fluoro-4-[(4',4'-dimethyl-8'-bromochroman-6'-yl)carbamoyl]benzo- ate (Compound 9), but using 2,2,4,4-tetramethyl-8-iodochromanoic acid (Compound X, 81 mg, 0.25 mmol) and ethyl 4-amino-2-fluorobenzoate ((Compound $C_1$, 55 mg, 0.30 mmol), the title compound was obtained as a white solid.

¹H NMR δ 8.05 (b, 1H), 8.01 (d, J=2.2 Hz, 1H), 7.94 (t, J=8.4 Hz, 1H), 7.86 (d, J=2.2 Hz, 1H), 7.75 (dd, J=12.88, 2.1 Hz, 1H), 7.33 (dd, J=8.8, 2.1 Hz, 1H), 4.37 (q, J=7.1 Hz, 2H), 1.89 (s, 2H), 1.42 (s, 6H), 1.38 (s, 6H).

Ethyl 2-Fluoro-4-[(2',2',4',4',8'-pentamethylchroman- 6'-yl)carbamoyl]benzoate (Compound 21)

Using the same procedure as for ethyl 2-fluoro-4-((4',4'-dimethyl-8'-bromochroman-6'-yl)carbamoyl]benzo- ate (Compound 9), but using 2,2,4,4,8-pentamethyl-6-chromanoic acid (Compound $A_1$, 92 mg, 0.37 mmol) and ethyl 4-amino-2-fluorobenzoate (Compound $C_1$, 75 mg, 0.41 mmol), the title compound was obtained as a white solid (100 mg).

¹H NMR δ 8.31 (b, 1H), 7.90 (t, J=8.24 Hz, 1H), 7.76 (dd, J=14.29, 1.7 Hz, 1H), 7.74 (s, 1H), 7.43 (s, 1H), 7.35 (dd, J=8.67, 1.7 Hz, 1H), 4.32 (q, J=7.1 Hz, 2H), 2.18 (s, 3H), 1.84 (s, 2H), 1.38 (t, J=7.1 Hz, 3H), 1.35 (s, 6H), 1.34 (s, 6H).

Ethyl 2-Fluoro-4-[(2',2',4',4'-tetramethylthiochroman-6'-yl) carbamoyl]benzoate (Compound 23)

Using the same procedure as for the synthesis of ethyl 2-fluoro-4-[(4',4'-dimethyl-8'-bromochroman-6'-yl)carbamoyl]benzoate (Compound 9) but using 2,2,4,4-tetramethyl- 6-thiochromanoic acid (15 mg, 0.06 mmol) and ethyl 2-fluoro-4-aminobenzoate (Compound C., 11.2 mg, 0.06 mmol), the title compound was obtained as colorless oil.

¹H NMR δ 7.95 (m, 2H), 7.75 (d, J=12.75 Hz, 1H), 7.58 (m, 2H), 7.50 (d, J=8.8 Hz, 1H), 7.28 (dd, J=10.6, 1.9 Hz, 1H), 4.38 (q, J=7.1 Hz, 2H), 1.99 (s, 2H), 1.44 (s, 6H), 1.42 (s, 6H), 1.40 (t, J=7.1 Hz, 3H).

Ethyl 4-[(5',6',7',8'-tetrahydro-5',5',8',8'-tetramethyl-2-naphthalenyl)thiocarbamoyl]benzoate (Compound 25)

To a solution of ethyl 4-[(5',6',7',8'-tetrahydro- 5',5',8', 8'-tetramethylnaphthalen-2-yl)carbamoyl]benzoate (Compound $I_1$, 61 mg, 0.16 mmol) in 2 ml of anhydrous benzene was added Lawesson's reagent (45 mg, 0.112 mmol). The resulting yellow solution was refluxed under N for 2 h. The solvent was removed and the residue was purified by column chromatography (silica gel, ethyl acetate/hexane 1/5) to give the title compound as a yellow solid (55 mg, 87%).

¹H NMR δ 9.04 (b, 1H), 8.11 (d, J=8.70 Hz, 2H), 7.85 (b, 2H), 7.75 (b, 1H), 7.55 (dd, J=8.2, 1.9 Hz, 1H), 7.36 (d, J=8.3 Hz, 1H), 4.38 (q, J=7.1 Hz, 2H), 1.71 (s, 4H), 1.40 (t, J=7.1 Hz, 3H), 1.30 (s, 12H).

Ethyl 2-Fluoro-4-[(5',6',7',8'-tetrahydro-5',5',8',8'-tetramethylnaphthalen-2'-yl)thiocarbamoyl]benzoate (Compound 27)

Using the same procedure as for the synthesis of ethyl 4-[(5',6',7',8'-tetrahydro-5',5',8',8'-tetramethyl-2-naphthalenyl)thiocarbamoyl]benzoate (Compound 25) but using ethyl 2-fluoro-4-[(5',6',7',8'-tetrahydro- 5',5',8',8'-tetramethylnaphthalen-2'- yl)carbamoyl]benzoate (Compound 1, 167 mg, 0.42 mmol) in 8 ml of benzene and Lawensson's reagent (220 mg, 0.544 mmol), the title compound was obtained as a bright yellow solid (127.5 mg).

$^1$H NMR δ 9.30 (b, 1H), 8.05 (b, 1H), 7.95 (t, J=8.37 Hz, 1H), 7.77 (d, J=1.89 Hz, 1H), 7.53 (dd, J=8.24, 2.1 Hz, 1H), 7.49 (b, 1H), 7.35 (d, J=8.24 Hz, 1H), 4.33 (g, J=7.1 Hz, 1H), 1.71. (s, 4H), 1.32 (s, 6H), 1.30 (s, 6H).

3-Hydroxy-5,5,8,8-tetramethyl-5,6,7,8-tetrahydronaphthalen-2-yl carboxylic acid (Compound L)

To a solution of 2-bromo-3-methoxymethoxy-5,5,8,8-tetrahydro-5,5,8,8-tetramethylnaphthalene (Compound J, 722 mg, 2.2 mmol) in 10 ml of dry THF at −78° C. under argon was added slowly 2.86 ml of t-BuLi (1.7 M in hexane, 4.8 mmol). The reaction mixture was stirred at −78° C. for 1 h. Then $CO_2$ was bubbled through the solution for 1 h. After removal of $CO_2$ stream, the reaction mixture was stirred for an additional hour at −78° C. Then 10% of HCl was added. After warming up to room temperature, the reaction mixture was left overnight then extracted with ethyl acetate. The organic layer was washed with brine and dried over $Na_2SO_4$. After concentration, the residue was purified by column chromatography (ethyl acetate/hexane 1/3) to yield the title compound as a white solid.

$^1$H NMR d 7.85 (s, 1H), 6.93 (s, 1H), 1.68 (s, 4H), 1.28 (s, 12H).

4-Bromo-3-hydroxy-5,5,8,8-tetramethyl-5,6,7,8-tetrahydronaphthalen-2-yl carboxylic acid (Compound M)

3-Hydroxy-5,5,8,8-tetramethyl-5,6,7,8-tetrahydronaphthalen-2-yl acid (Compound L, 155 mg, 0.62 mmol) was dissolved in 1 ml of HOAc. To this solution was added $Br_2$ (0.033 ml, 0.62 mmol). The reaction mixture was left at room temperature for over night. A stream of air was passed through the reaction mixture to remove the unreacted $Br_2$. The remaining solid was dissolved in small amount of THF and purified by column chromatography (ethyl acetate/hexane 1/1) to yield the desired product as a cream colored solid.

$^1$H NMR d 7.91 (s, 1H), 1.75 (m, 2H), 1.64 (m, 2H), 1,62 (s, 6H), 1.30 (s, 6H).

4-Bromo-3-methoxymethoxy-5,5,8,8-tetramethyl-5,6,7,8-tetrahydronaphthalen-2-yl carboxylic acid (Compound N)

To a solution of 4-bromo-3-hydroxy-5,5,8,8-tetramethyl-5,6,7,8-tetrahydronaphthalen-2-yl acid (Compound M), 233 mg, 0.71 mmol) in 6 ml of $CH_2Cl_2$ was added chloromethyl methyl ether (0.162 ml, 2.1 mmol), diisopropylethyl amine (0.764 ml, 4.2 mmol) and a catalytic amount of tetrabutylammouimn bromide. The reaction mixture was heated to 45° C. for 2 h. The reaction mixture was concentrated and the residue was purified by column chromatography (ethyl acetate/hexane 1/9) to yield the methoxymethyl ester of the title compound as a white solid (200 mg). This white solid was further dissolved in 20 ml of EtOH. An aqueous solution of NaOH (0.5 ml, 1M) was added. The reaction mixture was stirred at room temperature for over night. The EtOH was removed and the residue was added 2 ml of ethyl acetate and 3 ml of water. This mixture was very slowly acidified with 10% HCl to PH =7. The ethyl acetate layer was separated and washed with brine, dried over $Na_2SO_4$. After filtration of the drying agent and removal of solvent, the reaction yielded the title compound as a white solid (155 mg). $^1$H NMR d 7.99 (s, 1H), 5.20 (s, 2H), 3.66 (s, 3H), 1.74 (m, 2H), 1.67 (m, 2H), 1.60 (s, 6H), 1.32 (s, 6H).

Ethyl 2-fluoro-4-[(3'-methoxymethoxy-4'-bromo- 5',6',7',8'-tetrahydro-5',5',8',8'-tetramethylnaphthalen-2'-yl) carbamoyl]benzoate (Compound B.)

To a solution of 4-bromo-3-methoxymethoxy-5,5,8,8-tetramethyl-5,6,7,8-tetrahydronaphthalen-2-yl acid (Compound N, 80 mg, 0.22 mmol) in 4 ml of $CH_2Cl_2$ was added DMAP (60 mg, 0.26 mmol), ethyl 2-fluoro-4-aminobenzoate (Compound $C_1$, 43 mg, 0.24 mmol) and EDC (50 mg, 0.26 mmol). The reaction mixture was stirred at room temperature for overnight and then concentrated to dryness. The residue was purified by column chromatography (ethyl acetate/hexane 1/3) to yield the title compound as a clear oil (45 mg).

$^1$H NMR d 9.92 (b, 1H), 8.10 (s, 1H), 7.94 (t, J=8.4 15 Hz, 1H), 7.81 (dd, J=12.9; 1.9 Hz, 1H), 7.35 (dd, J=8.5; 1.8 Hz, 1H), 5.20 (s, 2H), 4.39 (q, J=7.1 Hz, 2H), 3.61 (s, 3H), 1.74 (m, 2H), 1.64 (m, 2H), 1.60 (s, 6H), 1.40 (t, J=7.1 Hz, 3H), 1.34 (s, 6H).

Methyl 2,6-Difluoro-4-[(3'-methoxymethoxy-4'-bromo-5',6',7',8'-tetrahydro-5',5',8',8'-tetramethylnaphthalen-2'-yl) carbamoyl]benzoate (Compound $M_1$)

Using the same procedure as for the synthesis of compound ethyl 2-fluoro-4-[(3'-methoxymethoxy-4'-bromo-5',6',7',8'-tetrahydro-5',5',8',8'-tetramethylnaphthalen-2'-yl) carbamoyl]benzoate (Compound Sl) but using 4-bromo-3-methoxymethoxy-5,5,8,8-tetramethyl-5,6,7,8-tetrahydronaphthalen-2-yl acid (Compound N, 80 mg, 0.22 mmol), DMAP (60 mg, 0.26 mmol), methyl 2,6-difluoro-4-aminobenzoate (Compound $H_1$, 52 mg, 0.24 mmol) and EDC (50 mg, 0.26 mmol), the title compound was obtained as a clear oil.

$^1$H NMR d 10.01 (b, 1H), 8.11 (s, 1H), 7.42 (d, J=10.0 Hz, 2H), 5.2 (s, 2H), 3.95 (s, 3H), 3.63 (s, 3H), 1.75 (m, 2H), 1.65 (m, 2H), 1.61 (S, 6H), 1.35 (S, 6H).

General procedure for the syntheses of benzoic acid derivatives by hydrolyzing the corresponding methyl or ethyl esters.

To a solution of ester (3.0 mmol) in 20 ml of EtOH was added 5 ml of 1 N NaOH in water. The reaction mixture was stirred at room temperature for overnight and neutralized with 10% HCl to PH=5. The alcohol was removed by evaporation and the aqueous layer was extracted with ethyl acetate (3×10 ml). The combined ethyl acetate layers were washed with $NaHCO_3$ (sat.), brine and dried over $MgSO_4$. After concentration, the desired acid was obtained which could be recrystallized in ethyl acetate or in acetonitrile.

2-Fluoro-4-[(5',6',7',8'-tetrahydro-5',5',8',8'-tetramethylnaphthalen-2'-yl)carbamoyl]benzoic Acid (Compound 2)

$^1$H NMR δ (acetone-$D_6$) 9.86 (b, 1H), 7.95 (m, 3H), 7.75 (dd, J=7.9, 2.2 Hz, 1H), 7.62 (dd, J=8.5, 1.6 Hz, 1H), 7.50 (d, J=8.3 Hz, 1H), 1.73 (s, 4H), 1.32 (s, 6H), 1.30 (s, 6H).

4-[(3'-Fluoro-5',6',7',8'-tetrahydro-5',5',8',8'-tetramethylnaphthalen-2'-yl)carbamoyl]benzoic Acid (Compound 4)

$^1$H NMR δ (acetone-$D^6$) 9.50 (b, 1H), 8.04 (b, 2H), 7.90 (b, 2H), 7.78 (d, J=7.81 Hz, 1H), 7.19 (d, J=12.3 Hz, 1H), 1.72 (s, 4H), 1.30 (s, 12H).

2-Fluoro-4-[(4'-bromo-5',6',7',8'-tetrahydro- 5',5',8',8'-tetramethylnaphthalen-2'- yl)carbamoyl]benzoic Acid (Compound 6)

$^1$H NMR δ (acetone-$D_6$) 9.97 (b, 1H), 8.04 (d, J=1.89 Hz, 1H), 8.01 (d, J=1.90 Hz, 1H), 7.95 (t, J=8.55 Hz, 1H), 7.90

(dd, J=12.28, 2.0 Hz, 1H), 7.59 (dd, J =8.67, 1.50 Hz, 1H), 1.76 (m, 4H), 1.58 (s, 6H), 1.35 (s, 6H).

2-Fluoro-4-[(3'-hydroxy-5',6',7',8'-tetrahydro- 5',5',8',8'-tetramethylnaphthalen-2'- yl)carbamoyl]benzoic Acid (Compound 8)

$^1$H NMR (acetone-$D_6$) 6 11.3 (b, 1H), 10.2 (b, 1H), 7.94 (m. 2H), 7.85 (dd, J=11.4, 1.95 Hz, 1H), 7.53 (dd, J=6.59, 2.08 Hz, 1H), 6.94 (s, 1H), 2.85 (b, 1H), 1.70 (s, 4H), 1.29 (s, 6H), 1.28 (s, 12H).

2-Fluoro-4-[(8'-bromo-4',4'-dimethylchroman-6'-yl)carbamoyl]benzoic Acid (Compound 10)

$^1$H NMR (acetone-$d_6$) 6 9.87 (b, 1H), 8.04 (d, J=2.1 Hz, 1H), 8.03 (d, J=2.1 Hz, 1H), 7.94 (t, J=8.66 Hz, 1H), 7.91 (dd, J=13.8, 2.0 Hz, 1H), 7.57 (dd, J=8.6, 2.0 Hz, 1H), 4.37 (t, J=5.44 Hz, 2H), 1.92 (t, J=5.44 Hz, 2H), 1.40 (s, 6H).

2-Fluoro-4-[(2',2',4',4'-tetramethyl-8'-bromochroman- 6'-yl)carbamoyl]benzoic Acid (Compound 12)

$^1$H NMR δ (acetone-$d_6$) 9.87 (b, 1H), 8.06 (d, J=2.2 Hz, 1H), 8.04 (d, J=2.1 Hz, 1H), 7.94 (t, J=8.54 Hz, 1H), 7.91 (dd, J=14.0, 2.0 Hz, 1H), 7.59 (dd, J - 8.5, 2.3 Hz, 1H), 1.96 (s, 2H), 1.42 (s, 6H), 1.41 (s, 6H).

2-Fluoro-4-[(2',2',4',4'-tetramethyl-8'-trifluoromethylchroman-6'-yl)carbamoyl]benzoic Acid (Compound 14)

$^1$H NMR (acetone-$d_6$) 6 10.02 (b, 1H), 8.31 (s, 1H), 8.09 (s, 1H), 7.92 (m, 2H), 7.56 (d, J=7.69 Hz, 1H), 2.00 (s, 2H), 1.44 (s, 6H), 1.41 (s, 6H).

2-Fluoro-4-[(2',2',4',4'-tetramethyl-8'-azidochroman-6'-yl) carbamoyl]benzoic Acid (Compound 16)

$^1$H NMR δ 8.03 (t, J=8.4 Hz, 1H), 7.87 (b, 1H), 7.79 (dd, J=13, 2.0 Hz, 1H), 7.64 (d, J=2.2 Hz, 1H), 7.32 (dd, J=8.66, 1.9 Hz, 1H), 7.22 (d, J=2.1 Hz, 1H), 1.91 (s, 2H), 1.45 (s, 6H), 1.41 (s, 6H).

2,6-Difluoro-4-[(2',2',4',4'-tetramethyl-8'-trifluoromethylchroman-6'-yl)carbamoyl]benzoic acid (Compound 18)

$^1$H NMR (acetone-$d_6$) 6 8.30 (d, J=2.3 Hz, 1H), 8.06 (d, J=2.2 Hz, 1H), 7.59 (d, J=10.32 Hz, 2H), 1.954 (s, 2H), 1.44 (s, 6H), 1.41 (s, 6H).

2-Fluoro-4-[(2',2',4',4'-tetramethyl-8'-iodochroman-6'-yl)carbamoyl]benzoic Acid (Compound 20)

$^1$H NMR δ (acetone-$d_6$) 10.0 (b, 1H), 8.24 (s, 1H), 8.07 (s, 1H), 7.94 (m, 2H), 7.57 (d, J=8.67 Hz, 1H), 1.95 (s, 2H), 1.41 (s, 12H).

2-Fluoro-4-[(2',2',4',4',8'-pentamethylchroman-6'-yl)carbamoyl]benzoic Acid (Compound 22)

$^1$H NMR δ (acetone-$d_6$) 9.77 (b, 1H), 7.90 (m, 3H), 7.65 (d, J=2.0 Hz, 1H), 7.56 (dd, J=8.61, 2.0 Hz, 1H), 2.19 (s, 3H), 1.90 (s, 2H), 1.38 (s, 6H), 1.37 (s, 6H).

2-Fluoro-4-[(2',2',4',4'-tetramethylthiochroman-6'-yl)carbamoyl]benzoic acid (Compound 24)

$^1$H NMR δ 7.95 (m, 2H), 7.75 (d, J=12.75 Hz, 1H), 7.58 (m, 2H), 7.50 (d, J=8.8 Hz, 1H), 7.28 (dd, J=10.6, 1.9 Hz, 1H), 1.99 (s, 2H), 1.44 (s, 6H), 1.42 (s, 6H).

4-[(5',6',7',8'-tetrahydro-5',5',8',8'-tetramethylnaphthalen-2'-yl)thiocarbamoyl]benzoic Acid (Compound 26)

$^1$H NMR δ 9.08 (b, 1H), 8.17 (d, J=8.61, 2H), 7.95 (b, 2H), 7.77 (b, 1H), 7.57 (dd, J=8.1, 2.1 Hz, 1H), 7.37 (d, J=8.2 Hz, 1H), 1.72 (s, 4H), 1.32 (s, 6H), 1.31 (s, 6H).

2-Fluoro-4-[(5',6',7',8'-tetrahydro-5',5',8',8'-tetramethylnaphthalen-2'-yl)thiocarbamoyl]benzoic Acid (Compound 28)

$^1$H NMR δ (acetone-$d_6$) 11.1 (b, 1H), 8.27 (b, J=13.2 Hz, 1H), 8.02 (t, J=8.3 Hz, 1H), 7.89 (S, 1H), 7.86 (d, J=10.0 Hz, 1H), 7.62 (d, J=8.3 Hz, 1H), 7.41 (d, J=8.37 Hz, 1H), 1.72 (S, 4H), 1.30 (s, 12H).

2-Fluoro-4-[(3'-hydroxy-4'-bromo-5',6',7',8'-tetrahydro-5', 5',8',8'-tetramethylnaphthalen-21-yl)carbamoyl]benzoic Acid (Compound 34)

A solution of ethyl 2-fluoro-4-[(3'-methoxymethoxy-4'-bromo-5',6',7',8'-tetrahydro-5',5',8',8'-tetramethylnaphthalen-2'-yl)carbamoyl]benzoate (Compound $S_1$, 45 mg, 0.084 mmol) in 1 ml of EtOH was added 1 ml of aqueous solution of NaOH (1M). The reaction mixture was stirred at room temperature for overnight and acidified to PH =1 with 10% HCl. EtOH was removed and ethyl acetate and more water were added to the solution. The organic layer was separated and washed with $NaHCO_3$, brine and dried over $MgSO_4$. After filtration and concentration, the reaction yielded 2-fluoro-4-[(3'-methoxymethoxy-4'-bromo-5', 6', 7', 8'- tetrahydro-5', 5', 8', 8'-tetramethylnaphthalen-2'- yl)carbamoyl]benzoic acid as a white solid. The methoxymethyl group was removed by dissolving the white solid in 2 ml of MeOH and 3 drops of HCl (con.). After stirring for overnight, the reaction mixture was concentrated to dryness. The residue was partitioned between ethyl acetate and water. The organic layer was separated, washed with $NaHCO_3$, brine and dried over $MgSO_4$. After filtration and concentration, the residual solid was purified in a mini (pipette) column with ethyl acetate/hexane (1/1) to give the title compound as a white solid (5.0 mg).

$^1$H NMR d (acetone-$d^6$) 10.19 (b, 1H), 8.01 (s, 1H), 7.96 (t, J=8.6 Hz, 1H), 7.76 (dd, J=11.2; 2.0 Hz, 1H), 7.54 (dd, J=8.8; 2.0 Hz, 1H), 1.75 (m, 2H), 1.65 (m, 2H), 1.61 (s, 6H), 1.32 (S, 6H).

2,6-Difluoro-4-[-(3-hydroxy-4'-bromo-5',6',7',8'-tetrahydro-5',5',8',8'-tetramethylnaphthalen-2I-yl)carbamoyl]benzoic Acid (Compound 36)

Using the same procedure as for the synthesis of 2-fluoro-4-[(3'-hydroxy-4'-bromo-5', 6', 7', 8'-tetrahydro-5', 5', 8', 8'-tetramethylnaphthalen-21-yl)carbamoyl]benzoic acid (Compound 34) the title compound was obtained as a white solid.

$^1$H NMR d(acetone-$d^6$) 10.23 (b, 1H), 8.01 (s, 1H), 7.52 (d, J=10.2 Hz, 2H), 4.8 (b, 1H), 1.75 (m, 2H), 1.65 (m, 2H), 1.60 (s, 6H), 1.31 (s, 6H).

2,6-Difluoro-4-[(5',6',7',8'-tetrahydro-5',5', 8', 8'-tetramethylnaphthalen-2'-yl)carbamoyl]benzoic Acid (Compound 38)

To 5,5,8,8-tetramethyl-5,6,7,8-tetrahydro-2-naphthoic acid (43 mg, 0.19 mmol) was added 1 ml of thionyl chloride. This mixture was refluxed for 2 h. Excess thionyl chloride was removed under reduced pressure and the residue was dissolved in 2 ml of $CH_2Cl_2$. To this solution was added methyl 4-amino-2,6-difluorobenzoate (Compound $H_1$, 7 mg, 0.2 mmol) followed by 0.5 ml of pyridine. The reaction mixture was stirred at room temperature for 4 h and was concentrated under reduced pressure. The residue was purified by column chromatography (ethyl acetate/hexane 1/5) to give the methyl ester of the desired product as a colorless oil.

$^1$H NMR d 8.11 (d, J=1.9 Hz, 1H), 8.05 (b, 1H), 7.86 (dd, J=6.2, 2.2 Hz, 1H), 7.41 (m, 3H), 3.93 (s, 3H), 1.69 (s, 4H), 1.29 (s, 6H), 1.28 (s, 6H). This color- less oil was hydrolyzed to the desired product with $NaOH/H_2O/EtOH$ according to the general procedure.

$^1$H NMR d (acetone-$d^6$) 9.74 (b, 1H), 7.95 (s, 1H), 7.70 (d, J=6.8 Hz, 1H), 7.43 (d, J=8.4 Hz, 3H), 1.71 (s, 4H), 1.29 (s, 6H), 1.28 (s, 6H).

Methyl 2-nitro-4-[(4'-bromo-5',6',7',8'-tetrahydro- 5',5',8',8'-tetramethylnaphthalen-2'- yl)carbamoyl]benzoate (Compound 29)

Using the same procedure as for the synthesis of Compound 1, but using Compound F and Compound $F_1$, the desired product was obtained as a white solid.

¹H NMR δ 9.24 (b, 1H), 9.23 (d, J=1.8 Hz, 1H), 7.92 (dd, J=8.4, 2.4, Hz, 1H), 7.87 (d, J=2.1 Hz, 1H), 7.84 (d, 3=2.1 Hz, 1H), 7.80 (d, J=8.7 Hz, 1H), 3.91 (s, 3H), 1.75 (m, 2H), 1.65 (m, 2H), 1.58 (s, 3H), 1.33 (s, 3H).

2-Nitro-4-[(4'-bromo-5',6',7',8'-tetrahydro- 5',5',8',8'-tetramethylnaphthalen-2'- yl)carbamoyl]benzoic acid (Compound 30) 6

¹H NMR δ (acetone-d ): 10.16 (b, 1H), 8.42 (d, J=2.0 Hz, 1H), 8.09 (dd, J=8.6; 2.1 Hz, 1H), 8.06 (di J=2.2 Hz, 1H), 8.04 (d, J=2.2 Hz, 1H), 7.93 (d, J=8.6 Hz, 1H), 1.75 (m, 2H), 1.65 (m, 2H), 1.57 (s, 3H), 1.34 (s, 3H).

What is claimed is:

1. A compound of the formula

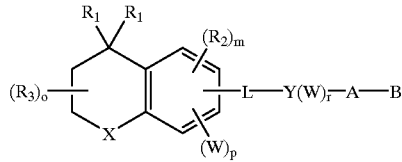

wherein X is $(C(R_1)_2)_n$ where n is an integer between 0 and 2;

$R_1$ is independently H or alkyl of 1 to 6 carbons;

$R_2$ is independently hydrogen, or lower alkyl of 1 to 6 carbons;

$R_3$ is independently hydrogen, lower alkyl of 1 to 6 carbons or F;

m is an integer having the value of 0–2;

o is an integer having the value of 0–4;

p is an integer having the value of 0–2;

r is an integer having the value 0–2 with the proviso that when Z is O the sum of p and r is at least 1;

Y is heteroaryl selected from a group consisting of furyl, pyridazinyl, pyrimidinyl, pyrazinyl, thiazolyl, oxazolyl, and imidazolyl said heteroaryl groups being optionally substituted with one or two $R_2$ groups;

W is a substituent selected from the group consisting of F, Br, Cl, I, $C_{1-6}$ alkyl, fluoro substituted $C_{1-6}$ alkyl, $NO_2$, $N_3$, OH, $OCH_2CH_3$, $OCH_2OCH_3$, $OC_{1-10}$alkyl, tetrazol, CN, $SO_2C_{1-6}$-alkyl, $SO_2C_{1-6}$-alkyl, $SO_2C_{1-6}$-fluoro substituted alkyl, $SO-C_{1-6}$ alkyl, $CO-C_{1-6}$alkyl, $COOR_8$, phenyl, phenyl itself substituted with a W group other than with phenyl or substituted phenyl;

L is —(C=Z)—NH— or —HN—(C=Z)—

Z is O or S;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound in accordance with claim 1 where A-B is $(CH_2)_q$—COOH or a pharmaceutically acceptable salt thereof, $(CH_2)_q$—$COOR_8$, or $(CH_2)_q$—$CONR_9R_{10}$.

* * * * *